United States Patent [19]

Böttcher et al.

[11] Patent Number: 4,824,852

[45] Date of Patent: Apr. 25, 1989

[54] SUBSTITUTED INDOLE COMPOUNDS WHICH HAVE USEFUL EFFECTS ON THE CENTRAL NERVOUS SYSTEM

[75] Inventors: Henning Böttcher, Darmstadt; Hans-Heinrich Hausberg, Ober-Ramstadt; Christoph Seyfried, Seeheim-Jugenheim; Klaus-Otto Minck, Ober-Ramstadt, all of Fed. Rep. of Germany

[73] Assignee: Merck Patent Gesellschaft mit Beschrankter Haftung, Darmstadt, Fed. Rep. of Germany

[21] Appl. No.: 153,692

[22] Filed: Feb. 8, 1988

Related U.S. Application Data

[62] Division of Ser. No. 878,559, Jun. 26, 1986, Pat. No. 4,740,602.

[30] Foreign Application Priority Data

Jun. 27, 1985 [DE] Fed. Rep. of Germany ....... 3522959

[51] Int. Cl.⁴ ..................... A61K 31/44; C07D 231/02
[52] U.S. Cl. .................................... 514/290; 514/291; 546/80; 546/89; 546/93; 546/101; 546/111; 546/79
[58] Field of Search ....................... 546/79, 80, 89, 93, 546/101, 111; 514/290, 291

[56] References Cited

U.S. PATENT DOCUMENTS

| | | | |
|---|---|---|---|
| 3,767,659 | 10/1959 | Suh | 546/80 |
| 4,034,095 | 7/1977 | Bastian | 546/93 |
| 4,081,543 | 3/1978 | Bastian | 546/101 |

Primary Examiner—Mary C. Lee
Assistant Examiner—Zinna Northington
Attorney, Agent, or Firm—Millen & White

[57] ABSTRACT

New indole derivatives of the general formula I

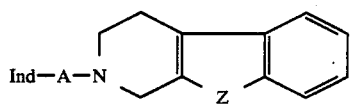

in which
Ind is a 3-indolyl radical which can be substituted by a hydroxymethyl, methylenedioxy, S-alkyl, SO-alkyl, $SO_2$-alkyl, CN or COW group and/or can be substituted once or twice by alkyl, O-alkyl, OH, F, Cl or Br,
is H, OH, O-alkyl, $NH_2$, NH-alkyl or $N(alkyl)_2$,
is $-(CH_2)_n-$, $-CH_2-S-CH_2CH_2-$, $-CH_2-SO-CH_2CH_2-$ or $-CH_2-SO_2-CH_2CH_2-$,
Z is $-(CH_2)_m-$, $-CH=CH-$, $-CHOH-$, $-CO-$, S, SO, $SO_2$ or O,
is 2, 3, 4 or 5 and
is 1, 2 or 3, in which the alkyl groups each have 1-4 C atoms, and their salts,
have effects on the central nervous system.

22 Claims, No Drawings

SUBSTITUTED INDOLE COMPOUNDS WHICH HAVE USEFUL EFFECTS ON THE CENTRAL NERVOUS SYSTEM

This is a division of application Ser. No. 878,559 filed June 26, 1986, now U.S. Pat. No. 4,740,602.

This invention relates to a new indole derivatives having pharmacological properties.

SUMMARY OF THE INVENTION

It is an object of this invention to provide new compounds which can be used for the preparation of medicaments.

Upon further study of the specification and appended claims, further objects and advantages of this invention will become apparent to those skilled in the art.

These objects have been achieved by providing new indole derivatives of the general formula I

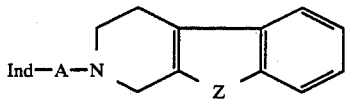

in which

Ind is a 3-indolyl radical which can be substituted by a hydroxymethyl, methylenedioxy, S-alkyl, SO-alkyl, $SO_2$-alkyl, CN or COW group and/or can be substituted once or twice by alkyl, O-alkyl, OH, F, Cl or Br, W is H, OH, O-alkyl, $NH_2$, NH-alkyl or N(alkyl)$_2$, A is $-(CH_2)_n-$, $-CH_2-S-CH_2CH_2-$, $-CH_2-SO-CH_2CH_2-$ or $-CH_2-SO_2-CH_2CH_2-$, Z is $-(CH_2)_m-$, $-CH=CH-$, $-CHOH-$, $-CO-$, S, SO, $SO_2$ or O, n is 2, 3, 4 or 5 and m is 1, 2 or 3, in which the alkyl groups each have 1–4 C atoms, and to their salts.

DETAILED DISCUSSION

It has been found that the compounds of the formula I and their physiologically acceptable salts have valuable pharmacological properties. Thus, they exhibit, in particular, effects on the central nervous system, especially dopamine-stimulating presynaptic (neuroleptic) or postsynaptic (anti-Parkinson) effects. Specifically, the compounds of the formula I induce contralateral pivoting behavior in hemiparkinsonian rats (which can be determined by the method of Ungerstedt et al., Brain Res. 24 (1970), 485–493) and inhibit the binding of tritiated dopamine agonists and antagonists to striatal receptors (which can be determined by the method of Schwarcz et al., J. Neurochemistry 34 (1980), 772–778, and Creese et al., European J. Pharmacol. 46 (1977), 377–381). In addition, the compounds inhibit the linguomandibular reflex of anaesthetized rats (which can be determined by a method based on that of Barnett et al., European J. Pharmacol. 21 (1973), 178–182, and of Ilhan et al., European J. Pharmacol. 33 (1975), 61–64). Furthermore, analgesic and hypotensive effects occur; thus, the blood pressure measured directly in conscious, spontaneously hypertensive rats (strain: SHR/NIH-MO/CHB-EMD; for method, compare Weeks and Jones, Proc. Soc. Exptl. Biol. Med. 104 (1960), 646–648) fitted with catheters is reduced after intragastric administration of the compounds.

Hence, the compounds of the formula I and their physiologically acceptable salts can be used as active compounds in medicaments and as intermediates for the preparation of other active compounds in medicaments.

The invention relates to the indole derivatives of the formula I and to their salts.

Alkyl in the radicals Ind and W is preferably methyl, as well as ethyl, n-propyl, isopropyl, n-butyl, isobutyl, sec.-butyl or tert.-butyl. O-Alkyl is preferably methoxy, as well as ethoxy, n-propoxy, isopropoxy, n-butoxy, isobutoxy, sec.-butoxy or tert.-butoxy. S-Alkyl is preferably methylthio, as well as ethylthio, propylthio, isopropylthio, butylthio, isobutylthio, sec.-butylthio or tert.-butylthio. SO-Alkyl is preferably methylsulfinyl, as well as ethyl-, propyl-, isopropyl-, butyl-, isobutyl-, sec.-butyl- or tert.-butylsulfinyl, and $SO_2$-alkyl is preferably methylsulfonyl, as well as ethyl-, propyl-, isopropyl-, butyl-, isobutyl-, sec.-butyl- or tert.-butylsulfonyl.

The radical Ind is, in particular, an unsubstituted or singly substituted 3-indolyl radical. It is preferably substituted in the 5- or 6-position or in the 4- or 7-position. Substitution in the 1- or 2-position is also possible. Preferred disubstituted 3-indolyl radicals are substituted in the 5,6-position; disubstitution is also possible in the 1,2-, 1,4-, 1,5-, 1,6-, 1,7-, 2,4-, 2,5-, 2,6-, 2,7-, 4,5-, 4,6-, 4,7-, 5,7- or 6,7-position. In all these cases, the substituents can be identical or different.

Specifically preferred substituents in the benzene ring of the radical Ind are hydroxyl and methoxy, as well as methyl, ethyl, ethoxy, F, Cl, Br, methylthio, methylsulfinyl, methylsulfonyl, CN, hydroxymethyl, formyl, carboxyl, methoxycarbonyl or ethoxycarbonyl, carbamoyl, N-methyl-, N-ethyl, N,N-dimethyl- and N,N-diethylcarbamoyl, as well as the other alkyl, O-alkyl, S-alkyl, SO-alkyl or $SO_2$-alkyl groups indicated above, as well as propoxy-, isopropoxy-, butoxy-, isobutoxy-, sec.-butoxy- and tert.-butoxycarbonyl, N-propyl-, N-isopropyl-, N-butyl-, N-isobutyl-, N-sec.-butyl-, N-tert.-butyl-, N-methyl-N-ethyl-, N,N-dipropyl-, N-methyl-N-propyl-, N-ethyl-N-propyl- and N,N-dibutylcarbamoyl. Accordingly, some preferred meanings of the radical Ind are, in particular, 5-hydroxy-3-indolyl, also 2-, 4-, 6- or 7-hydroxy-3-indolyl, unsubstituted 3-indolyl, 2-, 4-, 5-, 6- or 7-methoxy-3-indolyl, furthermore 1-, 2-, 4-, 5-, 6- or 7-methyl-3-indolyl, 1-, 2-, 4-, 5-, 6- or 7-ethyl-3-indolyl, 2-, 4-, 5-, 6- or 7-ethoxy-3-indolyl, 2-, 4-, 5-, 6- or 7-fluoro-3-indolyl, 2-, 4-, 5-, 6- or 7-chloro-3-indolyl, 2-, 4-, 5-, 6- or 7-bromo-3-indolyl, 2-, 4-, 5-, 6- or 7-methylthio-3-indolyl, 2-, 4-, 5-, 6- or 7-methylsulfinyl-3-indolyl, 2-, 4-, 5-, 6- or 7-methylsulfonyl-3-indolyl, 2-, 4-, 5-, 6- or 7-formyl-3-indolyl, 2-, 4-, 5-, 6- or 7-carboxy-3-indolyl, 2-, 4-, 5-, 6- or 7-methoxycarbonyl-3-indolyl, 2-, 4-, 5-, 6- or 7-ethoxycarbonyl-3-indolyl, 2-, 4-, 5-, 6- or 7-carbamoyl-3-indolyl, 2-, 4-, 5-, 6- or 7-N-methylcarbamoyl-3-indolyl, 2-, 4-, 5-, 6- or 7-N-ethylcarbamoyl-3-indolyl, 2-, 4-, 5-, 6- or 7-N,N-dimethylcarbamoyl-3-indolyl, furthermore 5,6-dihydroxy-3-indolyl, 5-hydroxy-6-methoxy-3-indolyl, 5-methoxy-6-hydroxy-3-indolyl, 5,6-dimethoxy-3-indolyl, also 4,5-, 4,6-, 4,7-, 5,7- or 6,7-dihydroxy-3-indolyl, 4-hydroxy-5-, 6- or 7-methoxy-3-indolyl, 5-hydroxy-4- or 7-methoxy-3-indolyl, 6-hydroxy-4- or 7-methoxy-3-indolyl, 7-hydroxy-4-, 5- or 6-methoxy-3-indolyl, 5,6-methylenedioxy-3-indolyl, 4,5-, 4,6-, 4,7-, 5,7- or 6,7-dimethoxy-3-indolyl, 1-methyl-4-, -5-, -6- or 7-hydroxymethyl-3-indolyl, 1-methyl-4-, -5-, -6- or -7-formyl-3-indolyl, 1- methyl-4-, -5-, -6- or -7-carboxy-3-indolyl, 1-methyl-4-, -5-, -6- or -7-carbamoyl-3-indolyl, 2-methyl-4-, -5-, -6- or -7-hydroxymethyl-3-indolyl, 2-methyl-4-, -5-, -6- or -7-formyl-3-indolyl, 2-methyl-4-, -5-, -6- or -7-carboxy-3-indolyl, 2-methyl-4-, -5-, -6- or -7-carbamoyl-3-indolyl, 5-methoxy-4-, -6- or -7-methoxycarbonyl-3-indolyl, 5-methoxy-4-, -6- or -7-ethoxycarbonyl-3-indolyl, 5-methoxy-4-, -6- or -7-carboxy-3-indolyl, 5-methoxy-4-, -6- or -7-carbamoyl-3-indolyl, 5-fluoro-4-, -6- or -7-carboxy-3-indolyl, 5-chloro-4-, -6- or 7-carboxy-3-indolyl, 7-chloro-4-, -5- or -6-carboxy-3-indolyl, 5-bromo-4-, -6- or -7-carboxy-3-indolyl, 5-hydroxy-4-, -6- or -7-methoxycarbonyl-3-indolyl, 5-hydroxy-4-, -6- or -7-ethoxycarbonyl-3-indolyl, 5-hydroxy-4-, -6- or -7-carboxy-3-indolyl, 5-hydroxy-4-, -6- or -7-carbamoyl-3-indolyl, 5-hydroxy-2-, -4-, -6- or -7-hydroxymethyl-3-indolyl, 6-hydroxy-4-, -5- or -7-carboxy-3-indolyl, 6-hydroxy-2-, -4-, -5- or -7-hydroxymethyl-3-indolyl.

The parameter n is preferably 4, and the radical A is preferably —(CH$_2$)$_4$— or —CH$_2$—S—CH$_2$CH$_2$—, and furthermore is preferably —(CH$_2$)$_2$—, —(CH$_2$)$_3$— or —(CH$_2$)$_5$—.

The parameter m is preferably 2. The radical Z is preferably —(CH$_2$)$_2$—, —CHOH—, S or O.

Accordingly, the invention particularly relates to those compounds of the formula I in which at least one of the radicals mentioned has one of the meanings indicated above, in particular one of the preferred meanings indicated above. Some preferred groups of compounds can be expressed by the following part formulae Ia to Il, which correspond to the formula I and in which the radicals and parameters which are not detailed having the meaning indicated in formula I, but in which in Ia Ind is hydroxy-3-indolyl, methoxy-3-indolyl or 3-indolyl, the substituents preferably being in the 5- or 6-position;
in Ib Ind is 5- or 6-hydroxy-3-indolyl, 5- or 6-methoxy-3-indolyl or 3-indolyl;
in Ic A is —(CH$_2$)$_n$— or —CH$_2$—S—CH$_2$CH$_2$—;
in Id A is —(CH$_2$)$_4$—;
in Ie Z is —(CH$_2$)$_2$;
in Ie' Z is —CH=CH—;
in If Z is —CHOH—;
in Ig Z is S;
in Ih Z is O;
in Ii Ind is 5- or 6-hydroxy-3-indolyl, 5- or 6-methoxy-3-indolyl or 3-indolyl,
 A is —(CH$_2$)$_n$— or —CH$_2$—S—CH$_2$CH$_2$— and
 Z is —(CH$_2$)$_2$;
in Ij Ind is 5- or 6-hydroxy-3-indolyl, 5- or 6-methoxy-3-indolyl or 3-indolyl,
 A is —(CH$_2$)$_n$— or —CH$_2$—S—CH$_2$CH$_2$— and
 Z is —CHOH;
in Ik Ind is 5- or 6-hydroxy-3-indolyl, 5- or 6-methoxy-3-indolyl or 3-indolyl,
 A is —(CH$_2$)$_n$— or —CH$_2$—S—CH$_2$CH$_2$— and
 Z is S;
in Il Ind is 5- or 6-hydroxy-3-indolyl, 5- or 6-methoxy-3-indolyl or 3-indolyl,
 A is —(CH$_2$)$_n$— or —CH$_2$—S—CH$_2$CH$_2$— and
 Z is O.

The compounds of the formula I can have one or more asymmetric carbon atoms. Thus they may be in the form of racemates if several asymmetric carbon atoms are present as well as mixtures of several racemates, and in various optically active forms.

The invention furthermore relates to a process for the preparation of the compounds of the formula I and of their salts, characterized in that a compound of the formula II Ind-A-X$^1$     II in which
X$^1$ is X or NH$_2$, and
X is Cl, Br, I, OH or a reactive functionally modified OH group, and
Ind and A have the indicated meanings,
is reacted with a compound of the formula III

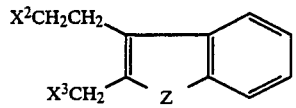     III in which
X$^2$ and X$^3$ can be identical or different and, where X$^1$ is NH$_2$, are each X, otherwise together they are NH and
Z has the indicated meaning,
or in that a compound which otherwise corresponds to formula I but has in place of one or more hydrogen atoms one or more reducible group(s) and/or one or more additional C—C and/or C—N bond(s) is treated with a reducing agent,
or in that a compound which otherwise corresponds to formula I but has in place of one or more hydrogen atoms or in place of an OH group one or more solvolysable group(s) is treated with a solvolysing agent,
or in that for the preparation of thioethers of the formula I in which A is —CH$_2$—S—CH$_2$CH$_2$—, a compound of the formula IV Ind-CH$_2$N(R)$_2$     IV in which
R is alkyl having 1–4 C atoms, and both radicals R are together also —(CH$_2$)$_p$— or —CH$_2$CH$_2$OCH$_2$CH$_2$—, and
p is 4 or 5, and
Ind has the indicated meaning,
is reacted with a thiol of the general formula V

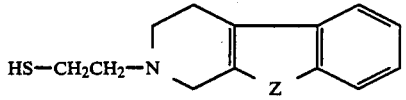     V in which Z has the indicated meaning, or one of its salts, and/or in that, where appropriate, a thioether group in a compound of the formula I is oxidized to an SO group or SO$_2$ group, or an SO group is oxidized to an SO$_2$ group, and/or an alkoxy group is cleaved with the formation of an OH group, and/or one COW group or CN group is converted by oxidation, reduction, esterification, amidation or solvolysis into one (other) COW group, and/or a COW group or CO group is reduced to a hydroxymethyl or to a CHOH or CH$_2$ group respectively, and/or a hydroxymethyl or CHOH group is oxidized to a CHO or COOH group or a CO group respectively, and/or in that a resulting base of the formula I is converted by treatment with an acid into one of its acid addition salts, or an acid of the formula I is converted by treatment with a base into one of its metal or ammonium salts.

The compounds of the formula I are otherwise prepared by methods known per se, as are described in the literature (for example in the standard works such as Houben-Weyl, Methoden der Organischen Chemie (Methods of Organic Chemistry) published by Georg Thieme, Stuttgart; Organic Reactions, John Wiley & Sons, Inc., New York), specifically under reaction conditions as are known and suitable for the conversions mentioned. It is also possible for this to make use of variants which are known per se but which are not mentioned here in detail.

The starting material for the claimed process can also, if desired, be formed in situ in such a manner that they are not isolated from the reaction mixture but are immediately reacted further to give the compounds of the formula I.

$X^1$ in the indole derivatives of the formula II is preferably X; accordingly, $X^2$ and $X^3$ in the compounds of the formula III are preferably together NH. The radical X is preferably Cl or Br; however, it can also be I, OH or a reactive functionally modified OH group, in particular alkylsulfonyloxy having 1-6 (for example methanesulfonyloxy) or arylsulfonyloxy having 6-10, C atoms (for example benzenesulfonyloxy, p-toluenesulfonyloxy, 1- or 2-naphthalenesulfonyloxy).

Accordingly, the indole derivatives of the formula I can be obtained, in particular, by reaction of compounds of the formula Ind-A-Cl or Ind-A-Br with compounds of the formula III in which $X^2$ and $X^3$ are together an NH group (hereinafter designated IIIa).

Some of the compounds of the formulae II and III are known; the compounds of the formulae II and III which are not known can readily be prepared in analogy to the known compounds. Compounds of the formula II (A=—$CH_2$—S—$CH_2CH_2$—) can be prepared from, for example, Mannich bases of the formula IV and thiols of the formula HS—$CH_2CH_2$—$X^1$, for example HS—$CH_2CH_2OH$. The sulfoxides and sulfones of the formula II (A=—$CH_2$—SO—$CH_2CH_2$— or —$CH_2$—$SO_2$—$CH_2CH_2$—) can be obtained in oxidation of the thioethers (II, A=—$CH_2$—S—$CH_2CH_2$—). Primary alcohols of the formula Ind-A-OH can be obtained by, for example, reduction of the corresponding carboxylic acids or their esters. Treatment with thionyl chloride, hydrogen bromide, phosphorus tribromide or similar halogenated compounds provides the corresponding halides of the formula Ind-A-Hal. The corresponding sulfonyloxy compounds can be obtained from the alcohols Ind-A-OH by reaction with the appropriate sulfonyl chlorides.

The iodine compounds of the formula Ind-A-I can be obtained, by, for example, the action of potassium iodide on the relevant p-toluenesulfonic esters. The amines of the formula Ind-A-$NH_2$ can be prepared, for example, from the halides using potassium phthalimide or by reduction of the corresponding nitriles.

Some of the compounds IIIa are known [compare Can. J. Chem. 52, 2316-26 (1984); Arch. Pharm. 309, 279-88 (1976)] and can be obtained, for example, by reaction of compounds of the formula VI

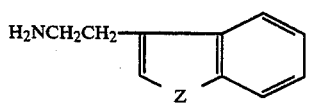

VI with formaldehyde.

Compounds of the formula III ($X^2$ and $X^3$ are both X) can be prepared by, for example, reduction of diesters of the formula VII

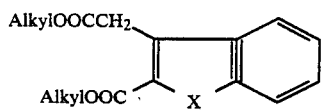

VII to diols of the formula III, $X^2=X^3=OH$, and, where appropriate, subsequent reaction with $SOCl_2$ or $PBr_3$.

The reaction of the compounds II and III takes place by methods as are known from the literature for the alkylation of amines. It is possible to melt the components together in the absence of a solvent, where appropriate in a sealed tube or in an autoclave. However, it is also possible to react the compounds in the presence of an inert solvent. Examples of suitable solvents are hydrocarbons, such as benzene, toluene and xylene; ketones such as acetone and butanone; alcohols such as methanol, ethanol, isopropanol and n-butanol; ethers such as tetrahydrofuran (THF) or dioxane; amides such as dimethylformamide (DMF) or N-methylpyrrolidone; nitriles such as acetonitrile, and, where appropriate, mixtures of these solvents with one another or mixtures with water. The addition of an acid-binding agent, for example in an alkali metal or alkaline earth metal hydroxide, carbonate or bicarbonate, or of another salt of a weak acid of the alkali metal or alkaline earth metals, preferably of potassium, sodium or calcium, or the addition of an organic base such as triethylamine, dimethylaniline, pyridine or quinoline, or of an excess of the amine component Ind-A-$NH_2$ or IIIa may be advantageous. The reaction time depends on the conditions used and is between a few minutes and 14 days, and the reaction temperature is between about 0° and 150°, normally between 20° and 130°.

It is also possible to obtain a compound of the formula I by treatment of a precursor, which contains in place of hydrogen atoms one or more reducible group(s) and/or one or more additional C—C and/or C—N bond(s), with a reducing agent, preferably at temperatures between −80° and +250° in the presence of at least one inert solvent.

Reducible groups (which can be replaced by hydrogen) are, in particular, oxygen in a carbonyl group, hydroxyl, arylsulfonyloxy (for example p-toluenesulfonyloxy(, N-benzenesulfonyl, N-benzyl or O-benzyl.

It is in principle possible to convert compounds which contain only one, or those, which contain two or more in justaposition, of the groups or additional bonds which are detailed above into a compound of the formula I by reduction; it is possible during this at the same time to reduce COW groups or CO groups contained in the starting compound. Use is made for this purpose preferably of nascent hydrogen or complex metal hydrides, as well as reduction by the Wolff-Kishner method.

Preferred starting materials for the reduction correspond to the formula VIII

Ind'-L-Q  VIII in which
Ind' is a 3-indolyl radical which can be substituted by a hydroxymethyl, methylenedioxy, S-alkyl, SO-alkyl, $SO_2$-alkyl, CN or COW group and/or can be substituted once or twice by alkyl, O-alkyl, OH, F, Cl, Br and/or O-benzyl and/or can be substituted in the 1-position by an arylsulfonyl group or a benzyl group, L is A or a chain corresponding to the radical A but in which one or more —CH$_2$ grou(s) have been replaced by —CO—, and/or more hydrogen atoms have been replaced by OH groups, Q is

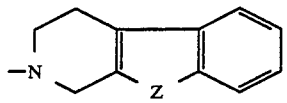

or

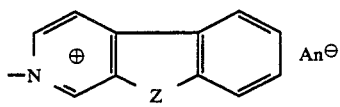

An$^-$ is an anion of a strong acid, and
Z has the abovementioned meaning,
but in which it is not possible at the same time for Ind' to be Ind, L to be A and Q to be

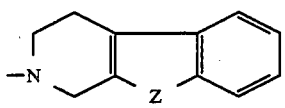

L in the compounds of the formula VIII is preferably —CO—(CH$_2$)$_{n-2}$—CO— [specifically —COCO—, —COCH$_2$CO—, —CO—(CH$_2$)$_2$—CO— or —CO—(CH$_2$)$_3$—CO—], —(CH$_2$)$_{n-1}$—CO—[specifically —CH$_2$CO—, —CH$_2$CH$_2$—CO—, —(CH$_2$)$_3$—CO— or —(CH$_2$)$_4$—CO—], —CH$_2$—S—CH$_2$—CO— or —CH$_2$—SO—CH$_2$—CO— or —CH$_2$—SO$_2$—CH$_2$—CO—, also, for example, —CO—CH$_2$CH$_2$—, —CH$_2$—CO—CH$_2$—, —CO—(CH$_2$)$_3$—, —CH$_2$—CO—CH$_2$CH$_2$—, —CH$_2$CH$_2$—CO—CH$_2$—, —CO—(CH$_2$)$_4$—, —CH$_2$—CO—(CH$_2$)$_3$—, —CH$_2$CH$_2$—CO—CH$_2$CH$_2$— or —(CH$_2$)$_3$—CO—CH$_2$—.

Compounds of the formula VIII can be prepared by, for example, reaction of IIIa or a compound of the formula IX with a compound of the formula X

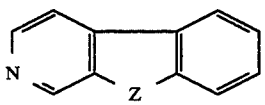      IX

Ind'—L—X$^1$      X in which Z, Ind', L and X$^1$ have the abovementioned meanings, under the conditions indicated above for the reaction of II with III.

If the reducing agent used is nascent hydrogen then this can be generated by, for example, treatment of metals with weak acids or with bases. Thus, for example, use can be made of a mixture of zinc with alkali metal hydroxide solution or of iron with acetic acid. It is also suitable to use sodium or another alkali metal in an alcohol such as ethanol, isopropanol, butanol, amyl or isoamyl alcohol or phenol. It is also possible to use an aluminum/nickel alloy in aqueous alkaline solution, where appropriate with the addition of ethanol. Sodium or aluminum amalgam in aqueous alcoholic or aqueous solution is also suitable for the generation of nascent hydrogen. The reaction can also be carried out in heterogeneous phase, use preferably being made of an aqueous phase and a benzene or toluene phase.

Reducing agents which can also be used in a particularly advantageous manner are complex metal hydrides such as LiAlH$_4$, NaBH$_4$, diisobutylaluminium hydride of NaAl-(OCH$_2$CH$_2$OCH$_3$)$_2$H$_2$ and diborane, if desired with the addition of catalysts such as BF$_3$, AlCl$_3$ or LiBr. Particularly suitable solvents for this purpose are ethers such as diethyl ether, di-n-butyl ether, THF, dioxane, diglyme of 1,2-dimethoxyethane, as well as hydrocarbons such as benzene. Primarily suitable solvents for a reduction with NaBH$_4$ are alcohols such as methanol or ethanol, as well as water and aqueous alcohols. Reductions by this method are preferably carried out at temperatures between −80° and +150°, in particular between about 0° and about 100°.

It is possible and particularly advantageous to reduce —CO-groups in acid amides or vinylogous acid amides (for example those of the formula VIII in which L is a —(CH$_2$)$_{n-1}$—CO—, —CH$_2$—S—CH$_2$—CO— or —CO—(CH$_2$)$_{n-2}$—CO— groups) to CH$_2$ groups with LiAlH$_4$ in THF at temperatures between about 0° and 66°. It is possible at the same time reductively to eliminate arylsulfonyl protective groups located in the 1-position of the indole ring, and/or to reduce groups Z=CO and/or COW groups located on the indole ring, for example CO groups to CHOH groups and/or COOalkyl, COOH or CHO groups to CH$_2$OH groups.

Reduction of the pyridinium salts of the formula VIII (in which Q is

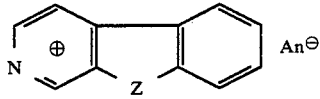

and An is preferably Cl, Br of CH$_3$SO$_3$) to compounds of the formula I takes place with, for example, NaBH$_4$ in water, methanol or ethanol or in mixtures of these solvents, if desired with the addition of a base, such as NaOH, at temperatures between about 0° and 80°.

N-Benzyl groups can be reductively eliminated with sodium in liquid ammonia.

It is also possible to reduce one or more carbonyl groups to CH$_2$ groups by the Wolff-Kishner method, for example by treatment with anhydrous hydrazine in absolute ethanol under pressure at temperatures between about 150° and 250°. The catalyst which is preferably used is sodium alcoholate. The reduction can also be carried out by the Huang-Minlon variation of the method by carrying out the reaction with hydrazine hydrate in a high-boiling solvent which is miscible with water, such as diethylene glycol or triethylene glycol, in the presence of alkali, such as sodium hydroxide. The reaction mixture is, as a rule, boiled for about 3–4 hours. The water is then removed by distillation, and the hydrazone which has formed is decomposed at temperatures up to about 200°. The Wolff-Kishner reduction can also be carried out with hydrazine in dimethyl sulfoxide at room temperature.

Compounds which otherwise correspond to formula I but contain in place of one or more H atoms one or more solvolysable group(s) can be solvolysed, in particular hydrolysed, to give the compounds of the formula I.

The starting materials for the solvolysis can be obtained by, for example, reaction of IIIa with compounds which correspond to the formula II ($X^1=X$) but contain in place of one or more H atoms one or more solvolysable group(s). Thus, in particular, 1-acylindole derivatives (corresponding to the formula I but containing an acyl group in the 1-position of the Ind radical, preferably an alkanoyl, alkylsulfonyl or arylsulfonyl group, in each case having up to 10 C atoms, such as methane-, benzene- or p-toluenesulfonyl) can be hydrolysed to the corresponding indole derivatives which are unsubstituted in the 1-position of the indole ring, for example in acid but better in neutral or alkaline medium at temperatures between 0° and 200°. Hydrolysis of compounds which correspond to the formula I but contain in place of the group Z a CHCl, CHBr or CHOacyl group (acyl being, for example, alkanoyl, aroyl, alkylsulfonyl or arylsulfonyl each having up to 10 C atoms) to compounds of the formula I ($Z=CHOH$) takes place analogously.

The basic catalysts which are preferably used for this are sodium, potassium or calcium hydroxide, sodium or potassium carbonate or ammonia. The solvent which is chosen is preferably water; lower alcohols such as methanol or ethanol; ethers such as THF or dioxane; sulfones such as tetramethylene sulfone; or their mixtures especially the mixtures containing water. Hydrolysis may even take place on treatment with water along, especially at the boiling point. A particularly mild process is the cleavage of trialkylsilyl ethers, in particular trimethyl- or dimethyl-tert.-butylsilyl ethers, using KF in methanol at about 10°–30°, the corresponding hydroxyl compounds being obtained.

Indole derivatives of the formula I ($A=-CH_2-S-CH_2CH_2-$) can also be obtained by reaction of Mannich bases of the formula IV with thiols of the formula V (or their salts).

Some of the starting materials of the formulae IV and V are known; those of the starting materials which are not known can readily be prepared in analogy to the known compounds. Thus, the Mannich bases of the formula IV can be obtained from, for example, indoles of the formula Ind-H, formaldehyde and amines of the formula $HN(R)_2$, and the thiols of the formula V can be obtained from the bases of the formula IIIa and thiol derivatives of the formula $HS-CH_2CH_2-X^1$ (it also being possible for there to be intermediate protection of the HS group).

Specifically, the reaction of IV with V takes place in the presence or absence of in inert solvent at temperatures between about −20° and 250°, preferably between 60° and 150°. Examples of suitable solvents are hydrocarbons such as benzene, toluene, xylenes or mesitylenes; tertiary bases such as triethylamine, pyridine or picolines; alcohols such as methanol, ethanol or butanol; glycols and glycol ethers such as ethylene glycol, diethylene glycol and 2-methoxyethanol; ketones such as acetone; ethers such as THF or dioxane; amides such as DMF; sulfoxides such as dimethyl sulfoxide. Mixtures of these solvents are also suitable. The thiols of the formula V are preferably initially converted into the corresponding mercaptides, preferably into the corresponding sodium or potassium mercaptides by reaction with sodium or potassium hydroxide or sodium or potassium ethylate.

It is furthermore possible, where appropriate, to convert a compound of the formula I into another compound of the formula I by methods which are known per se.

Thus, in a thioether of the formula I ($A=-CH_2-S-CH_2CH_2-$ or $Z=S$) the thioether group can be oxidized to an SO group or to an $SO_2$ group, or in a sulfoxide of the formula I ($A=-CH_2-SO-CH_2CH_2-$ or $Z=SO$) the SO group can be oxidized to an $SO_2$ group. If it is desired to obtain the sulfoxides then the oxidation is carried out with, for example, hydrogen peroxide, peracids such as m-chloroperbenzoic acid, Cr(VI) compounds such as chromic acid, $KMnO_4$, 1-chlorobenzotriazole, Ce(IV) compounds such as $(NH_4)_2\text{-}Ce(NO_3)_6$, negatively substituted aromatic diazonium salts such as o- or p-nitrophenyldiazonium chloride, or by electrolysis under relatively mild conditions and at relatively low temperatures (about −80° to +100°). If, on the other hand, it is desired to obtain the sulfones (from the thioethers or the sulfoxides) then the same oxidizing agents are used under more forcing conditions and/or in excess, and, as a rule, at higher temperatures. It is possible for the customary inert solvents to be present or absent in these reactions. Examples of suitable inert solvents are water, aqueous mineral acids, aqueous alkali metal hydroxide solutions, lower alcohols such as methanol or ethanol, esters such as ethyl acetate, ketones such as acetone, lower carboxylic acids such as acetic acid, nitriles such as acetonitrile, hydrocarbons such as benzene and chlorinated hydrocarbons such as chloroform or $CCl_4$. A preferred oxidizing agent is 30% aqueous hydrogen peroxide. When the calculated amount is used in solvents such as acetic acid, acetone, methanol, ethanol or aqueous sodium hydroxide solution, at temperatures between −20° and 100°, the latter results in the sulfoxides, and in excess at higher temperatures, preferably in acetic acid or in a mixture of acetic acid and acetic anhydride, the latter results in the sulfones.

Ethers of the formula I in which the radical Ind is substituted once or twice by O-alkyl can be cleaved to produce the corresponding hydroxyl derivatives. For example, the ethers can be cleaved by treatment with dimethyl sulfide/boron tribromide complex, for example in toluene, ethers such as THF, or dimethyl sulfoxide, or by fusion with pyridine hydrohalides or aniline hydrohalides, preferably pyridine hydrochloride, at about 150°–250°, or by treatment with diisobutylaluminum hydride in toluene at about 0°–110°.

It is furthermore possible to convert COW groups or CN groups into (other) COW groups by methods known per se. Thus, it is possible to oxidize aldehyde groups to carboxyl groups, for example with $MnO_2$ in an inert solvent such as dichloromethane. On the other hand, carboxyl groups can be reduced, for example with diisobutylaluminium hydride in toluene. Carboxyl groups can be esterified, for example by treatment with alcohols in the presence of an acid catalyst or by reaction with diazoalkanes. Conversion of the carboxylic acids into their chlorides, for example using $SOCl_2$, and subsequent reaction with $NH_3$ or amines results in the corresponding carboxamides, which can also be obtained by treatment of the carboxylic esters with ammonia or amines. Solvolysis, preferably hydrolysis under the conditions indicated above, converts nitriles into carboxamides or nitriles, esters or amides into carboxylic acids; in particular, carboxylic acids can be obtained from the carbamoyl compounds by treatment of the latter with NaOH of KOH in aqueous glycols or glycol ethers, for example diethylene glycol monomethyl or monoethyl ether, preferably at temperatures between about 50° and about 200°.

Reduction of COW, in particular formyl, alkoxycarbonyl or carboxyl groups, may also result in hydroxymethyl groups; it is possible analogously to reduce groups Z=CO to groups Z=CHOH. The reducing agent which is preferably used is a complex hydride such as LiAlH$_4$; aldehydes and esters can also be reduced with other reducing agents listed above. The conditions which are preferably used are those indicated above. Conversely, hydroxymethyl groups and CHOH groups can be oxidized, for example with MnO$_2$ or Ba(MnO$_4$)$_2$, to formyl or carboxyl groups and to CO groups respectively.

A base of the formula I which is obtained can be converted with an acid into the relevant acid addition salt. Acids which are suitable for this reaction are those which provide physiologically acceptable salts. Thus, it is possible to use inorganic acids, for example sulfuric acid, hydrohalic acids such as hydrochloric acid or hydrobromic acid, phosphoric acids such as orthophosphoric acid, nitric acid, and sulfamic acid, as well as organic acids, specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids, and lauryl sulfuric acid. Salts with physiologically unacceptable acids, for example picrates, can be used for the isolation or purification of the compounds of the formula I.

The free bases of the formula I can, if desired, be liberated from their salts by treatment with strong bases such as sodium or potassium hydroxide, or sodium or potassium carbonate.

On the other hand, it is possible to convert compounds of the formula I having free COOH groups into their metal or ammonium salts by reaction with bases. Particularly suitable salts are the sodium, potassium, magnesium, calcium and ammonium salts, as well as substituted ammonium salts, for example the dimethyl-, diethyl-, monoethanol-, diethanol-, triethanol-, cyclohexyl- or dicyclohexyl-ammonium salts.

All starting materials not specifically discussed above are known and/or can be prepared from known materials using conventional methods. The compounds of the formula I and their physiologically acceptable salts can be used for the preparation of pharmaceutical compositions, in particular by non-chemical means. This may entail them being converted into a suitable dosage form together with at least one solid, liquid or semi-liquid vehicle or auxilary and, where appropriate, in combination with one or more other active compound(s).

The invention also relates to agents, in particular pharmaceutical compositions, containing at least one compound of the formula I and/or one of its physiologically acceptable salts. These compositions can be used as medicaments in human or veterinary medicine. Suitable vehicles are organic or inorganic substances which are suitable for enteral (for example oral), parenteral or topical administration and which do not react with the new compounds, for example water, vegetable oils, benzyl alcohols, polyethylene glycols, gelatin, carbohydrates, such as lactose or starch, magnesium stearate, talc, and vaseline. Enteral administration is effected by, in particular, tablets, coated tablets, capsules, syrups, elixirs, drops or suppositories, parenteral administration is effected by solutions, preferably oily or aqueous solutions, as well as suspensions, emulsions or implants, and topical application is effected by ointments, creams or powders. The new compounds can also be freeze-dried, and the resulting lyophilizates can be used, for example, for the preparation of products for injection. The compositions which have been indicated can be sterilized and/or contain auxiliaries such as lubricants, preservatives, stabilizers and/or wetting agents, emulsifiers, salts to influence the osmotic pressure, buffer substances, coloarants, flavorings and/or aroma substances. They can, if desired, also contain one or more other active compounds, for example one or more vitamins.

The compounds of the formula I and their physiologically acceptable salts can be administered to humans or animals, in particular mammals such as monkeys, dogs, cats, rats or mice, and be used for the therapeutic treatment of the human or animal body and for controlling diseases, especially for the therapy of parkinsonism, of extrapyramidal disturbances associated with conventional neuroleptic therapy, of states of depression and/or psychosis and of side effects associated with the treatment of hypertension (for example with α-methyldopa). Furthermore, the compounds can be used in endocrinology and gynaecology, for example for the therapy of acromegaly, hypogonadism, secondary amenorrhoea, premenstrual syndrome, undesired puerperal lactation and generally as a prolactin inhibitor, also for the therapy of cerebral disturbances (for example migraine), especially in geriatrics similar to certain ergot alkaloids, as well as for reducing blood pressure.

As a rule this will entail the substances according to the invention being administered in analogy to known products which are commercially available (for example bromocriptine and dihydroergocornine), preferably in doses between about 0.2 and 500 mg, in particular between 0.2 and 50 mg, per dose unit. The daily dose is preferably between about 0.001 and 10 mg/kg body weight. The low doses (about 0.2 to 1 mg per dose unit; about 0.001 to 0.005 mg/kg body weight) are particularly suitable for use as agents for migraine; for the other indications doese between 10 and 50 mg per dose unit are preferred. More specifically, preferred dosage ranges for specific indications are as follows: parkinsonism 1 to 200, preferably 40 to 100; dyskinesia 40 to 100; psychosis, e.g., chronic schizophrenia 2 to 20; acromegaly 2 to 50 mg per dosage unit. However, the specific dose for each particular patient depends on a very wide variety of factors, for example, on the efficacy of the specific compound used, on the age, body weight, general state of health and the sex, on the diet, the timing and route of administration, on the rate of excretion, the medicament combination and the severity of the particular disorder for which the therapy is applied. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

In the examples which follow "normal working up" means if necessary water is added, extraction with dichloromethane is carried out, and the organic phase is separated off, dried over sodium sulfate and filtered, and the filtrate is evaporated, and the product is purified by chromatography on silica gel and/or by crystallization. Temperatures are reported in °C. Rf values were determined by thin-layer chromatography on silica gel.

EXAMPLE 1

A solution of 20.8 g of 3-(4-chlorobutyl)indole [or 25.2 g of 3-(4-bromobutyl)indole] and 18.9 g of 1,2,3,4-tetrahydrobenzothieno[2,3-c]pyridine in 100 ml of acetonitrile is stirred at 20° for 12 hours. The usual working up is carried out, and 2-[4-(3-indolyl)butyl]-1,2,3,4-tetrahydrobenzothieno[2,3-c]pyridine ("A"), m.p. 113°–115° is obtained.

The following 1,2,3,4-tetrahydrobenzothieno[2,3-c]pyridines are obtained analogously using the corresponding indole derivatives of the formula II ($X^1=X$):
2-[2-(3-indolyl)ethyl]-
2-[3-(3-indolyl)propyl]-
2-[4-(4-cyano-3-indolyl)butyl]-
2-[4-(5-cyano-3-indolyl)butyl]-
2-[4-(6-cyano-3-indolyl)butyl]-
2-[4-(7-cyano-3-indolyl)butyl]-
2-[4-(4-methoxycarbonyl-3-indolyl)butyl]-
2-[4-(5-methoxycarbonyl-3-indolyl)butyl]-
2-[4-(6-methoxycarbonyl-3-indolyl)butyl]-
2-[4-(7-methoxycarbonyl-3-indoly)butyl]-
2-[4-(4-ethoxycarbonyl-3-indolyl)butyl]-
2-[4-(5-ethoxycarbonyl-3-indolyl)butyl]-
2-[4-(6-ethoxycarbonyl-3-indolyl)butyl]-
2-[4-(7-ethoxycarbonyl-3-indolyl)butyl]-
2-[4-(4-carbamoyl-3-indolyl)butyl]-
2-[4-(5-carbamoyl-3-indolyl)butyl]-
2-[4-(6-carbamoyl-3-indolyl)butyl]-
2-[4-(7-carbamoyl-3-indolyl)butyl]-
2-[4-(5-N-methylcarbamoyl-3-indolyl)butyl]-
2-[4-(5-N,N-dimethylcarbamoyl-3-indolyl)butyl]-
2-[4-(1-methyl-3-indolyl)butyl]-
2-[4-(2-methyl-3-indolyl)butyl]-
2-[4-(5-methyl-3-indolyl)butyl]-
2-[4-(4-methoxy-3-indolyl)butyl]-
2-[4-(5-methoxy-3-indolyl)butyl -, Rf 0.45 (ethyl acetate)
2-[4-(6-methoxy-3-indolyl)butyl]-
2-[4-(7-methoxy-3-indolyl)butyl]-
2-[4-(5,6-dimethoxy-3-indolyl)butyl]-
2-[4-(4-hydroxy-3-indolyl(butyl]-
2-[4-(5-hydroxy-3-indolyl)butyl]-, m.p. 181°–183°
2-[4-(6-hydroxy-3-indolyl)butyl]-
2-[4-(7-hydroxy-3-indolyl)butyl]-
2-[4-(5,6-dihydroxy-3-indolyl)butyl]-
2-[4-(5-fluoro-3-indolyl)butyl]-
2-[4-(6-fluoro-3-indolyl)butyl]-
2-[4-(5-chloro-3-indolyl)butyl]-
2-[4-(6-chloro-3-indolyl)butyl]-
2-[4-(5-bromo-3-indolyl)butyl]-
2-[4-(6-bromo-3-indolyl)butyl]-
2-[5-(3-indolyl)pentyl]-.

EXAMPLE 2

In analogy to Example 1, 2-[4-(3-indolyl)butyl]-1,2,3,4-tetrahydrobenzofuro[2,3-c]pyridine is obtained using 1,2,3,4-tetrahydrobenzofuro[2,3-c]pyridine [m.p. 109° (decomposition); obtainable by reaction of 1-benzyl-3-piperidone with O-phenylhydroxylamine to give 2-benzyl-1,2,3,4-tetrahydrobenzofuro[2,3-c]pyridine and hydrogenolysis].

The following 1,2,3,4-tetrahydrobenzofuro[2,3-c]pyridines are obtained analogously:
3-[2-(3-indolyl)ethyl]-
3-[3-(3-indolyl)propyl]-
3-[4-(4-cyano-3-indolyl)butyl]-
3-[4-(5-cyano-3-indolyl)butyl]-
3-[4-(6-cyano-3-indolyl)butyl]-
3-[4-(7-cyano-3-indolyl)butyl]-
3-[4-(4-methoxycarbonyl-3-indolyl)butyl]-
3-[4-(5-methoxycarbonyl-3-indolyl)butyl]-
3-[4-(6-methoxycarbonyl-3-indolyl)butyl]-
3-[4-(7-methoxycarbonyl-3-indolyl)butyl]-
3-[4-(4-ethoxycarbonyl-3-indolyl)butyl]-
3-[4-(5-ethoxycarbonyl-3-indolyl)butyl]-
3-[4-(6-ethoxycarbonyl-3-indolyl)butyl]-
3-[4-(7-ethoxycarbonyl-3-indolyl)butyl]-
3-[4-(4-carbamoyl-3-indolyl)butyl]-
3-[4-(5-carbamoyl-3-indolyl)butyl]-
3-[4-(6-carbamoyl-3-indolyl)butyl]-
3-[4-(7-carbamoyl-3-indolyl)butyl]-
3-[4-(5-N-methylcarbamoyl-3-indolyl)butyl]-
3-[4-(5-N,N-dimethylcarbamoyl-3-indolyl)butyl]-
3-[4-(1-methyl-3-indolyl)butyl]-
3-[4-(2-methyl-3-indolyl)butyl]-
3-[4-(5-methyl-3-indolyl)butyl]-
3-[4-(4-methoxy)-3-indolyl)butyl]-
3-[4-(5-methoxy-3-indolyl)butyl]- , Rf 0.5 (ethyl acetate)
3-[4-(6-methoxy-3-indolyl)butyl]-
3-[4-(7-methoxy-3-indolyl)butyl]-
3-[4-(5,6-dimethoxy-3-indolyl)butyl]-
3-[4-(4-hydroxy-3-indolyl)butyl]-
3-[4-(5-hydroxy-3-indolyl)butyl]-, m.p. 173°–175°
3-[4-(6-hydroxy-3-indolyl)butyl]-
3-[4-(7-hydroxy-3-indolyl)butyl]-
3-[4-(5,6-dihydroxy-3-indolyl)butyl]-
3-[4-(5-fluoro-3-indolyl)butyl]-
3-[4-(6-fluoro-3-indolyl)butyl]-
3-[4-(5-chloro-3-indolyl)butyl]-
3-[4-(6-chloro-3-indolyl)butyl]-
3-[4-(5-bromo-3-indolyl)butyl]-
3-[4-(6-bromo-3-indolyl)butyl]-
3-[5-(3-indolyl)pentyl]-.

EXAMPLE 3

In analogy to Example 1 3-[4-(3-indolyl)butyl]-1,2,3,4,5,6-hexahydrobenzo[f]isoquinoline, m.p. 190°–192°, hydrochloride m.p. 198°–200°, is obtained using 1,2,3,4,5,6-hexahydrobenzo[f]isoquinoline.

The following 1,2,3,4,5,6-hexahydrobenzo[f]isoquinolines are obtained analogously:
3-[2-(3-indolyl)ethyl]-
3-[3-(3-indolyl)propyl]-
3-[4-(5,6-methylenedioxy-3-indolyl)-butyl]-, m.p. 133°–135°
3-[4-(4-cyano-3-indolyl)butyl]-
3-[4-(5-cyano-3-indolyl)butyl]-
3-[4-(6-cyano-3-indolyl)butyl]-
3-[4-(7-cyano-3-indolyl)butyl]-
3-[4-(4-methoxycarbonyl-3-indolyl)butyl]-

3-[4-(5-methoxycarbonyl-3-indolyl)butyl]-
3-[4-(6-methoxycarbonyl-3-indolyl)butyl]-
3-[4-(7-methoxycarbonyl-3-indolyl)butyl]-
3-[4-(4-ethoxycarbonyl-3-indolyl)butyl]-
3-[4-(5-ethoxycarbonyl-3-indolyl)butyl]-
3-[4-(6-ethoxycarbonyl-3-indolyl)butyl]-
3-[4-(7-ethoxycarbonyl-3-indolyl)butyl]-
3-[4-(4-carbamoyl-3-indolyl)butyl]-
3-[4-(5-carbamoyl-3-indolyl)butyl]-
3-[4-(6-carbamoyl-3-indolyl)butyl]-
3-[4-(7-carbamoyl-3-indolyl)butyl]-
3-[4-(5-N-methylcarbamoyl-3-indolyl)butyl]-
3-[4-(5-N,N-dimethylcarbamoyl-3-indolyl)butyl]-
3-[4-(1-methyl-3-indolyl)butyl]-
3-[4-(2-methyl-3-indolyl)butyl]-
3-[4-(5-methyl-3-indolyl)butyl]-
3-[4-(4-methoxy-3-indolyl)butyl]-
3-[4-(5-methoxy-3-indolyl)butyl]-
3-[4-(6-methoxy-3-indolyl)butyl]-
3-[4-(7-methoxy-3-indolyl)butyl]-
3-[4-(5,6-dimethoxy-3-indolyl)butyl]-
3-[4-(4-hydroxy-3-indolyl)butyl]-
3-[4-(5-hydroxy-3-indolyl)butyl]-, m.p. 184°–186°
3-[4-(6-hydroxy-3-indolyl)butyl]-
3-[4-(7-hydroxy-3-indolyl)butyl]-
3-[4-(5,6-dihydroxy-3-indolyl)butyl]-
3-[4-(5-fluoro-3-indolyl)butyl]-
3-[4-(6-fluoro-3-indolyl)butyl]-
3-[4-(5-chloro-3-indolyl)butyl]-
3-[4-(6-chloro-3-indolyl)butyl]-
3-[4-(5-bromo-3-indolyl)butyl]-
3-[4-(6-bromo-3-indolyl)butyl]-
3-[5-(3-indolyl)pentyl]-.

EXAMPLE 4

In analogy to Example 1 2-[4-(3-indolyl)butyl]-1,2,3,4-tetrahydro-2-azafluorene is obtained using 1,2,3,4-tetrahydro-2-azafluorene [obtainable by reaction of 3-methylindene with ammonium acetate and formaldehyde to give 4a-methyl-1,2,3,4,4a,9a-hexahydro-2-aza-4-oxafluorene and treatment with HCl].

The following 1,2,3,4-tetrahydro-2-azafluorenes are obtained analogously:
2-[2-(3-indolyl)ethyl]-
2-[3-(3-indolyl)propyl]-
2-[4-(4-cyano-3-indolyl)butyl]-
2-[4-(5-cyano-3-indolyl)butyl]- 2-[4-(6-cyano-3-indolyl)butyl]-
2-[4-(7-cyano-3-indolyl)butyl]-
2-[4-(4-methoxycarbonyl-3-indolyl)butyl]-
2-[4-(5-methoxycarbonyl-3-indolyl)butyl]-
2-[4-(6-methoxycarbonyl-3-indolyl)butyl]-
2-[4-(7-methoxycarbonyl-3-indolyl)butyl]-
2-[4-(4-ethoxycarbonyl-3-indolyl)butyl]-
2-[4-(5-ethoxycarbonyl-3-indolyl)butyl]-
2-[4-(6-ethoxycarbonyl-3-indolyl)butyl]-
2-[4-(7-ethoxycarbonyl-3-indolyl)butyl]-
2-[4-(4-carbamoyl-3-indolyl)butyl]-
2-[4-(5-carbamoyl-3-indolyl)butyl]-
2-[4-(6-carbamoyl-3-indolyl)butyl]-
2-[4-(7-carbamoyl-3-indolyl)butyl]-
2-[4-(5-N-methylcarbamoyl-3-indolyl)butyl]-
2-[4-(5-N,N-dimethylcarbamoyl-3-indolyl)butyl]-
2-[4-(1-methyl-3-indolyl)butyl]-
2-[4-(2-methyl-3-indolyl)butyl]-
2-[4-(5-methyl-3-indolyl)butyl]-
2-[4-(4-methoxy-3-indolyl)butyl]-
2-[4-(5-methoxy-3-indolyl)butyl]-, m.p. 143°–145°
2-[4-(6-methoxy-3-indolyl)butyl]-
2-[4-(7-methoxy-3-indolyl)butyl]-
2-[4-(5,6-dimethoxy-3-indolyl)butyl]-
2-[4-(4-hydroxy-3-indolyl)butyl]-, m.p. 198°–201°
2-[4-(5-hydroxy-3-indolyl)butyl]-
2-[4-(6-hydroxy-3-indolyl)butyl]-
2-[4-(7-hydroxy-3-indolyl)butyl]-
2-[4-(5,6-dihydroxy-3-indolyl)butyl]-
2-[4-(5-fluoro-3-indolyl)butyl]-
2-[4-(6-fluoro-3-indolyl)butyl]-
2-[4-(5-chloro-3-indolyl)butyl]-
2-[4-(6-chloro-3-indolyl)butyl]-
2-[4-(5-bromo-3-indolyl)butyl]-
2-[4-(6-bromo-3-indolyl)butyl]-
2-[5-(3-indolyl)pentyl]-.

EXAMPLE 5

In analogy to Example 1 3-[4-(3-indolyl)butyl]-1,2,3,4,6,7-hexahydro-3-aza-5H-dibenzo[a,c]cycloheptene and 3-[4-(5-hydroxy-3-indolyl)butyl]-1,2,3,4-hexahydro-3-aza-5H-dibenzo[a,c]cycloheptene (m.p. 119°–121°) are obtained using 1,2,3,4,6,7-hexahydro-3-aza-5H-dibenzo[a,c]cycloheptene (obtainable by reaction of 3-methyl-6,7-dihydro-5H-benzocycloheptene with ammonium acetate and formaldehyde to give 11b-methyl-1,2,3,4,4a,6,7,11b-octahydro-3-aza-1-oxa-5H-dibenzo[a,c]cycloheptene and treatment with HCl).

EXAMPLE 6

In analogy to Example 1 2-[4-(3-indolyl)butyl]-1,2,3,4-tetrahydrobenzothieno[2,3-c]pyridine 5-oxide is obtained using 1,2,3,4-tetrahydrobenzothieno[2,3-c]pyridine 5-oxide (obtainable by boiling 1,2,3,4-tetrahydrobenzothieno[2,3-c]pyridine with 30% $H_2O_2$ in ethanol).

The S-oxides of the compounds mentioned in Example 1 are obtained analogously using the corresponding indole derivatives.

EXAMPLE 7

In analogy to Example 1 2-[4-(3-indolyl)butyl]-1,2,3,4-tetrahydrobenzothieno[2,3-c]pyridine S,S-dioxide is obtained using 1,2,3,4-tetrahydrobenzothieno[2,3-c]pyridine S,S-dioxide (obtainable by boiling 1,2,3,4-tetrahydrobenzothieno[2,3-c]pyridine with 30% $H_2O_2$ in acetic acid).

The S,S-dioxides of the compounds mentioned in Example 1 are obtained analogously using the corresponding indole derivatives.

EXAMPLE 8

In analogy to Example 1 2-[4-(3-indolyl)butyl]-hydroxy-1,2,3,4-tetrahydro-2-azafluorene, m.p. 205°–208°, is obtained using 9-hydroxy-1,2,3,4-tetrahydro-2-azafluorene (obtained by bromination of 1,2,3,4-tetrahydro-2-azafluorene with pyrrolidine hydrobromide-perbromide to give 9-bromo-1,2,3,4-tetrahydro-2-azafluorene and hydrolysis with KOH).

The following 9-hydroxy-1,2,3,4-tetrahydro-2-azafluorenes are obtained analogously:
2-[2-(3-indolyl)ethyl]-
2-[3-(3-indolyl)propyl]-
2-[4-(4-cyano-3-indolyl)butyl]-
2-[4-(5-cyano-3-indolyl)butyl]-
2-[4-(6-cyano-3-indolyl)butyl]-
2-[4-(7-cyano-3-indolyl)butyl]-
2-[4-(4-methoxycarbonyl-3-indolyl)butyl]-
2-[4-(5-methoxycarbonyl-3-indolyl)butyl]-

2-[4-(6-methoxycarbonyl-3-indolyl)butyl]-
2-[4-(7-methoxycarbonyl-3-indolyl)butyl]-
2-[4-(4-ethoxycarbonyl-3-indolyl)butyl]-
2-[4-(5-ethoxycarbonyl-3-indolyl)butyl]-
2-[4-(6-ethoxycarbonyl-3-indolyl)butyl]-
2-[4-(7-ethoxycarbonyl-3-indolyl)butyl]-
2-[4-(4-carbamoyl-3-indolyl)butyl]-
2-[4-(5-carbamoyl-3-indolyl)butyl]-
2-[4-(6-carbamoyl-3-indolyl)butyl]-
2-[4-(7-carbamoyl-3-indolyl)butyl]-
2-[4-(5-N-methylcarbamoyl-3-indolyl)butyl]-
2-[4-(5-N,N-dimethylcarbamoyl-3-indolyl)butyl]-
2-[4-(1-methyl-3-indolyl)butyl]-
2-[4-(2-methyl-3-indolyl)butyl]-
2-[4-(5-methyl-3-indolyl)butyl]-
2-[4-(4-methoxy-3-indolyl)butyl]-
2-[4-(5-methoxy-3-indolyl)butyl]-
2-[4-(6-methoxy-3-indolyl)butyl]-
2-[4-(7-methoxy-3-indolyl)butyl]-
2-[4-(5,6-dimethoxy-3-indolyl)butyl]-
2-[4-(4-hydroxy-3-indolyl)butyl]-
2-[4-(5-hydroxy-3-indolyl)butyl]-
2-[4-(6-hydroxy-3-indolyl)butyl]-
2-[4-(7-hydroxy-3-indolyl)butyl]-
2-[4-(5,6-dihydroxy-3-indolyl)butyl]-
2-[4-(5-fluoro-3-indolyl)butyl]-
2-[4-(6-fluoro-3-indolyl)butyl]-
2-[4-(5-chloro-3-indolyl)butyl]-
2-[4-(6-chloro-3-indolyl)butyl]-
2-[4-(5-bromo-3-indolyl)butyl]-
2-[4-(6-bromo-3-indolyl)butyl]-
2-[5-(3-indolyl)butyl]-.

EXAMPLE 9

In analogy to Example 1 2-[4-(3-indolyl)butyl]-9-oxo-1,2,3,4-tetrahydro-2-azafluorene is obtained using 9-oxo-1,2,3,4-tetrahydro-2-azafluorene (obtained from 9-hydroxy-1,2,3,4-tetrahydro-2-azafluorene and CrO$_3$).

The following 9-oxo-1,2,3,4-tetrahydro-2-azafluorenes are obtained analogously:
2-[2-(3-indolyl)ethyl]-
2-[3-(3-indolyl)propyl]-
2-[4-(4-cyano-3-indolyl)butyl]-
2-[4-(5-cyano-3-indolyl)butyl]-
2-[4-(6-cyano-3-indolyl)butyl]-
2-[4-(7-cyano-3-indolyl)butyl]-
2-[4-(4-methoxycarbonyl-3-indolyl)butyl]-
2-[4-(5-methoxycarbonyl-3-indolyl)butyl]-
2-[4-(6-methoxycarbonyl-3-indolyl)butyl]-
2-[4-(7-methoxycarbonyl-3-indolyl)butyl]-
2-[4-(4-ethoxycarbonyl-3-indolyl)butyl]-
2-[4-(5-ethoxycarbonyl-3-indolyl)butyl]-
2-[4-(6-ethoxycarbonyl-3-indolyl)butyl]-
2-[4-(7-ethoxycarbonyl-3-indolyl)butyl]-
2-[4-(4-carbamoyl-3-indolyl)butyl]-
2-[4-(5-carbamoyl-3-indolyl)butyl]-
2-[4-(6-carbamoyl-3-indolyl)butyl]-
2-[4-(7-carbamoyl-3-indolyl)butyl]-
2-[4-(5-N-methylcarbamoyl-3-indolyl)butyl]-
2-[4-(5-N,N-dimethylcarbamoyl-3-indolyl)butyl]-
2-[4-(1-methyl-3-indolyl)butyl]-
2-[4-(2-methyl-3-indolyl)butyl]-
2-[4-(5-methyl-3-indolyl)butyl]-
2-[4-(4-methoxy-3-indolyl)butyl]-
2-[4-(5-methoxy-3-indolyl)butyl]-
2-[4-(6-methoxy-3-indolyl)butyl]-
2-[4-(7-methoxy-3-indolyl)butyl]-
2-[4-(5,6-dimethoxy-3-indolyl)butyl]-
2-[4-(4-hydroxy-3-indolyl)butyl]-
2-[4-(5-hydroxy-3-indolyl)butyl]-
2-[4-(6-hydroxy-3-indolyl)butyl]-
2-[4-(7-hydroxy-3-indolyl)butyl]-
2-[4-(5,6-dihydroxy-3-indolyl)butyl]-
2-[4-(5-fluoro-3-indolyl)butyl]-
2-[4-(6-fluoro-3-indolyl)butyl]-
2-[4-(5-chloro-3-indolyl)butyl]-
2-[4-(6-chloro-3-indolyl)butyl]-
2-[4-(5-bromo-3-indolyl)butyl]-
2-[4-(6-bromo-3-indolyl)butyl]-
2-[5-(3-indolyl)pentyl]-.

EXAMPLE 10

A mixture of 1.88 g of 3-(4-aminobutyl)indole and 2.45 g of 2-chloromethyl-3-(2-chloroethyl)benzothiophene (obtainable by reduction of ethyl 2-ethoxycarbonylbenzothiophene-3-acetate with LiAlH$_4$ followed by reaction with SOCl$_2$) in 40 ml of acetone and 40 ml of water is boiled for 24 hours, and the usual working up is carried out. "A" is obtained, m.p. 113°–115°.

EXAMPLE 11

A suspension of 40.2 g of 2-[4-(5-methoxy-3-indolyl)-1,4-dioxobutyl]-1,2,3,4-tetrahydrobenzofuro[2,3-c]pyridine [obtainable from 4-(5-methoxy-3-indolyl)-4-oxobutyric acid and 1,2,3,4-tetrahydrobenzofuro[2,3-c]pyridine] in 3 l of hot absolute THF is added dropwise, with stirring, to a suspension of 23.4 g of LiAlH$_4$ in 1100 ml of absolute THF, and the mixture is boiled for 1 hour, cooled, and decomposition is carried out with water and sodium hydroxide solution, and the usual working up is carried out. 2-[4-(5-methoxy-3-indolyl)butyl]-1,2,3,4-tetrahydrobenzofuro[2,3-c]pyridine is obtained, Rf 0.5 (ethyl acetate).

The following is obtained analogously from 2-[4-(2-carboxy-3-indolyl)-1-oxobutyl-1,2,3,4-tetrahydrobenzofuro[2,3-c]pyridine:
2-[4-(2-carboxy-3-indolyl)butyl]-1,2,3,4-tetrahydrobenzofuro[2,3-c]pyridine.

EXAMPLE 12

1 g of NaBH$_4$ in 20 ml of water is added, with stirring, to a solution of 4.51 g of 1-[4-(5-methoxy-3-indolyl)butyl]benzofuro[2,3-c]pyridinium bromide [obtainable from 3-(4-bromobutyl)-5-methoxyindole and benzofuro[2,3-c]pyridine] in 50 ml of 1N NaOH, and the mixture is then stirred at 60° for 3 hours. After the usual working up, 2-[4-(5-methoxy-3-indolyl)butyl]-1,2,3,4-tetrahydrobenzofuro[2,3-c]pyridine is obtained, Rf 0.5 (ethyl acetate).

EXAMPLE 13

In analogy to Example 12, 2-[4-(3-indolyl)butyl]-9-hydroxy-1,2,3,4-tetrahydro-2-azafluorene, m.p. 205°–208°, is obtained from 2-[4-(3-indolyl)butyl]-9-oxoindeno[2,3-c]pyridinium bromide [obtainable from 3-(4-bromobutyl)indole and 2-azafluorenone] and excess NaBH$_4$.

EXAMPLE 14

A mixture of 36.9 g of 2-[4-(5-cyano-3-indolyl)butyl]-1,2,3,4-tetrahydrobenzofuro[2,3-c]pyridine (obtainable from the corresponding 5-formyl compound via the oxime), 27.1 g of NaOH, 520 ml of water and 420 ml of diethylene glycol monoethyl ether is stirred at a bath temperature of 140° for 3 hours. The mixture is cooled, the usual working up is carried out, and 2-[4-(5-carbamoyl-3-indolyl)butyl]-1,2,3,4-tetrahydrobenzofuro[2,3-c]pyridine is obtained.

EXAMPLE 15

The process is carried out as described in Example 14 but boiling is continued for 16 hours and, after the usual working up, 2-[4-(5-carboxy-3-indolyl)butyl]-1,2,3,4-tetrahydrobenzofuro[2,3-c]pyridine is obtained.

The following are obtained analogously by hydrolysis of the corresponding nitriles:
2-[4-(4-carboxy-3-indolyl)butyl]-1,2,3,4-tetrahydrobenzothieno[2,3-c]pyridine
2-[4-(5-carboxy-3-indolyl)butyl]-1,2,3,4-tetrahydrobenzothieno[2,3-c]pyridine
2-[4-(6-carboxy-3-indolyl)butyl]-1,2,3,4-tetrahydrobenzothieno[2,3-c]pyridine
2-[4-(7-carboxy-7-indolyl)butyl]-1,2,3,4-tetrahydrobenzothieno[2,3-c]pyridine
2-[4-(4-carboxy-3-indolyl)butyl]-1,2,3,4-tetrahydrobenzofuro[2,3-c]pyridine
2-[4-(6-carboxy-3-indolyl)butyl]-1,2,3,4-tetrahydrobenzofuro[2,3-c]pyridine
2-[4-(7-carboxy-3-indolyl)butyl]-1,2,3,4-tetrahydrobenzofuro[2,3-c]pyridine
3-[4-(4-carboxy-3-indolyl)butyl]-1,2,3,4,5,6-hexahydrobenzo[f]isoquinoline
3-[4-(5-carboxy-3-indolyl)butyl]-1,2,3,4,5,6-hexahydrobenzo[f]isoquinoline
3-[4-(6-carboxy-3-indolyl)butyl]-1,2,3,4,5,6-hexahydrobenzo[f]isoquinoline
3-[4-(7-carboxy-3-indolyl)butyl]-1,2,3,4,5,6-hexahydrobenzo[f]isoquinoline
2-[4-(4-carboxy-3-indolyl)butyl]-1,2,3,4-tetrahydro-2-azafluorene
2-[4-(5-carboxy-3-indolyl)butyl]-1,2,3,4-tetrahydro-2-azafluorene
2-[4-(6-carboxy-3-indolyl)butyl]-1,2,3,4-tetrahydro-2-azafluorene
2-[4-(7-carboxy-3-indolyl)butyl]-1,2,3,4-tetrahydro-2-azafluorene
2-[4-(4-carboxy-3-indolyl)butyl]-9-hydroxy-1,2,3,4-tetrahydro-2-azafluorene
2-[4-[5-carboxy-3-indolyl)butyl]-9-hydroxy-1,2,3,4-tetrahydro-2-azafluorene
2-[4-(6-carboxy-3-indolyl)butyl]-9-hydroxy-1,2,3,4-tetrahydro-2-azafluorene
2-[4-(7-carboxy-3-indolyl)butyl]-9-hydroxy-1,2,3,4-tetrahydro-2-azafluorene
2-[4-(4-carboxy-3-indolyl)butyl]-9-oxo-1,2,3,4-tetrahydro-2-azafluorene
2-[4-(5-carboxy-3-indolyl)butyl]-9-oxo-1,2,3,4-tetrahydro-2-azafluorene
2-[4-(6-carboxy-3-indolyl)butyl]-9-oxo-1,2,3,4-tetrahydro-2-azafluorene
2-[4-(7-carboxy-3-indolyl)butyl]-9-oxo-1,2,3,4-tetrahydro-2-azafluorene.

EXAMPLE 16

4.96 g of 3-[4-(1-benzenesulfonyl-3-indolyl)butyl]-1,2,3,4,5,6-hexahydrobenzo[f]isoquinoline [obtainable from 1-benzenesulfonyl-3-(4-chlorobutyl)indole and 1,2,3,4,5,6-hexahydrobenzo[f]isoquinoline] are boiled with 1 g of KOH in 7 ml of water and 14 ml of ethanol for 16 hours, and the mixture is concentrated, the usual working up is carried out, and 3-[4-(3-indolyl)butyl]-1,2,3,4,5,6-hexahydrobenzo[f]isoquinoline, m.p. 190°-192°, hydrochloride m.p. 198°-200°, is obtained.

EXAMPLE 17

2.76 g of Na are dissolved in 180 ml of ethanol, and 24.9 g of 2-(2-mercaptoethyl)-1,2,3,4-tetrahydrobenzothieno[2,3-c]pyridine [obtainable by reaction of 1,2,3,4-tetrahydrobenzothieno[2,3-c]pyridine with thioglycolic acid to give 2-(2-mercaptoacetyl)-1,2,3,4-tetrahydrobenzothieno[2,3-c]pyridine, and reduction with LiAlH$_4$] and 23.2 g of methyl gramine-5-carboxylate are added, and the mixture is boiled for 16 hours, evaporated and the usual working up is carried out, and 2-[4-(5-methoxycarbonyl-3-indolyl)-3-thiabutyl]-1,2,3,4-tetrahydrobenzothieno[2,3-c]pyridine is obtained.

From the appropriate starting materials of the formulae IV and V, the following 1,2,3,4-tetrahydrobenzothieno[2,3-c]pyridines are obtained analogously:
2-[4-(3-indolyl)-3-thiabutyl]-
2-[4-(4-cyano-3-indolyl)-3-thiabutyl]-
2-[4-(5-cyano-3-indolyl)-3-thiabutyl]-
2-[4-(6-cyano-3-indolyl)-3-thiabutyl]-
2-[4-(7-cyano-3-indolyl)-3-thiabutyl]-
2-[4-(4-methoxycarbonyl-3-indolyl)-3-thiabutyl]-
2-[4-(6-methoxycarbonyl-3-indolyl)-3-thiabutyl]-
2-[4-(7-methoxycarbonyl-3-indolyl)-3-thiabutyl]-
2-[4-(4-ethoxycarbonyl-3-indolyl)-3-thiabutyl]-
2-[4-(5-ethoxycarbonyl-3-indolyl)-3-thiabutyl]-
2-[4-(6-ethoxycarbonyl-3-indolyl)-3-thiabutyl]-
2-[4-(7-ethoxycarbonyl-3-indolyl)-3-thiabutyl]-
2-[4-(4-carbamoyl-3-indolyl)-3-thiabutyl]-
2-[4-(5-carbamoyl-3-indolyl)-3-thiabutyl]-
2-[4-(6-carbamoyl-3-indolyl)-3-thiabutyl]-
2-[4-(7-carbamoyl-3-indolyl)-3-thiabutyl]-
2-[4-(4-methoxy-3-indolyl)-3-thiabutyl]-
2-[4-(5-methoxy-3-indolyl)-3-thiabutyl]-
2-[4-(6-methoxy-3-indolyl)-3-thiabutyl]-
2-[4-(7-methoxy-3-indolyl)-3-thiabutyl]-
2-[4-(5-fluoro-3-indolyl)-3-thiabutyl]-
2-[4-(6-fluoro-3-indolyl)-3-thiabutyl]-
2-[4-(5-chloro-3-indolyl)-3-thiabutyl]-
2-[4-(6-chloro-3-indolyl)-3-thiabutyl]-
2-[4-(5-bromo-3-indolyl)-3-thiabutyl]-
2-[4-(6-bromo-3-indolyl)-3-thiabutyl]-;
and the following 1,2,3,4-tetrahydrobenzofuro[2,3-c]pyridines:
2-[4-(3-indolyl)-3-thiabutyl]-
2-[4-(4-cyano-3-indolyl)-3-thiabutyl]-
2-[4-(5-cyano-3-indolyl)-3-thiabutyl]-
2-[4-(6-cyano-3-indolyl)-3-thiabutyl]-
2-[4-(7-cyano-3-indolyl)-3-thiabutyl]-
2-[4-(4-methoxycarbonyl-3-indolyl)-3-thiabutyl]-
2-[4-(5-methoxycarbonyl-3-indolyl)-3-thiabutyl]-
2-[4-(6-methoxycarbonyl-3-indolyl)-3-thiabutyl]-
2-[4-(7-methoxycarbonyl-3-indolyl)-3-thiabutyl]-
2-[4-(4-ethoxycarbonyl-3-indolyl)-3-thiabutyl]-
2-[4-(5-ethoxycarbonyl-3-indolyl)-3-thiabutyl]-
2-[4-(6-ethoxycarbonyl-3-indolyl)-3-thiabutyl]-
2-[4-(7-ethoxycarbonyl-3-indolyl)-3-thiabutyl]-
2-[4-(4-carbamoyl-3-indolyl)-3-thiabutyl]-
2-[4-(5-carbamoyl-3-indolyl)-3-thiabutyl]-
2-[4-(6-carbamoyl-3-indolyl)-3-thiabutyl]-
2-[4-(7-carbamoyl-3-indolyl)-3-thiabutyl]-
2-[4-(4-methoxy-3-indolyl)-3-thiabutyl]-
2-[4-(5-methoxy-3-indolyl)-3-thiabutyl]-
2-[4-(6-methoxy-3-indolyl)-3-thiabutyl]-
2-[4-(7-methoxy-3-indolyl)-3-thiabutyl]-
2-[4-(5-fluoro-3-indolyl)-3-thiabutyl]-
2-[4-(6-fluoro-3-indolyl)-3-thiabutyl]-
2-[4-(5-chloro-3-indolyl)-3-thiabutyl]-

2-[4-(6-chloro-3-indolyl)-3-thiabutyl]-
2-[4-(5-bromo-3-indolyl)-3-thiabutyl]-
2-[4-6-bromo-3-indolyl)-3-thiabutyl]-;
and the following 1,2,3,4,5,6-hexahydrobenzo[f-]isoquinolines:
3-[4-(3-indolyl)-3-thiabutyl]-
3-[4-(4-cyano-3-indolyl)-3-thiabutyl]-
3-[4-(5-cyano-3-indolyl)-3-thiabutyl]-
3-[4-(6-cyano-3-indolyl)-3-thiabutyl]-
3-[4-(7-cyano-3-indolyl)-3-thiabutyl]-
3-[4-(4-methoxycarbonyl-3-indolyl)-3-thiabutyl]-
3-[4-(5-methoxycarbonyl-3-indolyl)-3-thiabutyl]-
3-[4-(6-methoxycarbonyl-3-indolyl)-3-thiabutyl]-
3-[4-(7-methoxycarbonyl-3-indolyl)-3-thiabutyl]-
3-[4-(4-ethoxycarbonyl-3-indolyl)-3-thiabutyl]-
3-[4-(5-ethoxycarbonyl-3-indolyl)-3-thiabutyl]-
3-[4-(6-ethoxycarbonyl-3-indolyl)-3-thiabutyl]-
3-[4-(7-ethoxycarbonyl-3-indolyl)-3-thiabutyl]-
3-[4-(4-carbamoyl-3-indolyl)-3-thiabutyl]-
3-[4-(5-carbamoyl-3-indolyl)-3-thiabutyl]-
3-[4-(6-carbamoyl-3-indolyl)-3-thiabutyl]-
3-[4-(7-carbamoyl-3-indolyl)-3-thiabutyl]-
3-[4-(4-methoxy-3-indolyl)-3-thiabutyl]-
3-[4-(5-methoxy-3-indolyl)-3-thiabutyl]-
3-[4-(6-methoxy-3-indolyl)-3-thiabutyl]-
3-[4-(7-methoxy-3-indolyl)-3-thiabutyl]-
3-[4-(5-fluoro-3-indolyl)-3-thiabutyl]-
3-[4-(6-fluoro-3-indolyl)-3-thiabutyl]-
3-[4-(5-chloro-3-indolyl)-3-thiabutyl]-
3-[4-(6-chloro-3-indolyl)-3-thiabutul]-
3-[4-(5-bromo-3-indolyl)-3-thiabutyl]-
3-[4-(6-bromo-3-indolyl)-3-thiabutyl]-;
and the following 1,2,3,4-tetrahydro-2-azafluorences:
2-[4-(3-indolyl)-3-thiabutyl]-
2-[4-(4-cyano-3-indolyl)-3-thiabutyl]-
2-[4-(5-cyano-3-indolyl)-3-thiabutyl]-
2-[4-(6-cyano-3-indolyl)-3-thiabutyl]-
2-[4-(7-cyano-3-indolyl)-3-thiabutyl]-
2-[4-(4-methoxycarbonyl-3-indolyl)-3-thiabutyl]-
2-[4-(5-methoxycarbonyl-3-indolyl)-3-thiabutyl -
2-[4-(6-methoxycarbonyl-3-indolyl)-3-thiabutyl]-
2-[4-(7-methoxycarbonyl-3-indolyl)-3-thiabutyl]-
2-[4-(4-ethoxycarbonyl-3-indolyl)-3-thiabutyl]-
2-[4-(5-ethoxycarbonyl-3-indolyl)-3-thiabutyl]-
2-[4-(6-ethoxycarbonyl-3-indolyl)-3-thiabutyl]-
2-[4-(7-ethoxycarbonyl-3-indolyl)-3-thiabutyl]-
2-[4-(4-carbamoyl-3-indolyl)-3-thiabutyl]-
2-[4-(5-carbamoyl-3-indolyl)-3-thiabutyl]-
2-[4-(6-carbamoyl-3-indolyl)-3-thiabutyl]-
2-[4-(7-carbamoyl-3-indolyl)-3-thiabutyl]-
2-[4-(4-methoxy-3-indolyl)-3-thiabutyl]-
2-[4-(5-methoxy-3-indolyl)-3-thiabutyl]-
2-[4-(6-methoxy-3-indolyl)-3-thiabutyl]-
2-[4-(7-methoxy-3-indolyl)-3-thiabutyl]-
2-[4-(5-fluoro-3-indolyl)-3-thiabutyl]-
2-[4-(6-fluoro-3-indolyl)-3-thiabutyl]-
2-[4-(5-chloro-3-indolyl)-3-thiabutyl]-
2-[4-(6-chloro-3-indolyl)-3-thiabutyl]-
2-[4-(5-bromo-3-indolyl)-3-thiabutyl]-
2-[4-(6-bromo-3-indolyl)-3-thiabutyl]-;
and the following 9-hydroxy-1,2,3,4-tetrahydro-2-azafluorenes:
2-[4-(3-indolyl)-3-thiabutyl]-
2-[4-(4-cyano-3-indolyl)-3-thiabutyl]-
2-[4-(5-cyano-3-indolyl)-3-thiabutyl]-
2-[4-(6-cyano-3-indolyl)-3-thiabutyl]-
2-[4-(7-cyano-3-indolyl)-3-thiabutyl]-
2-[4-(4-methoxycarbonyl-3-indolyl)-3-thiabutyl]-
2-[4-(5-methoxycarbonyl-3-indolyl)-3-thiabutyl]-
2-[4-(6-methoxycarbonyl-3-indolyl)-3-thiabutyl]-
2-[4-(7-methoxycarbonyl-3-indolyl)-3-thiabutyl]-
2-[4-(4-ethoxycarbonyl-3-indolyl)-3-thiabutyl]-
2-[4-(5-ethoxycarbonyl-3-indolyl)-3-thiabutyl]-
2-[4-(6-ethoxycarbonyl-3-indolyl)-3-thiabutyl]-
2-[4-(7-ethoxycarbonyl-3-indolyl)-3-thiabutyl]-
2-[4-(4-carbamoyl-3-indolyl)-3-thiabutyl]-
2-[4-(5-carbamoyl-3-indolyl)-3-thiabutyl]-
2-[4-(6-carbamoyl-3-indolyl)-3-thiabutyl]-
2-[4-(7-carbamoyl-3-indolyl)-3-thiabutyl]-
2-[4-(4-methoxy-3-indolyl)-3-thiabutyl]-
2-[4-(5-methoxy-3-indolyl)-3-thiabutyl]-
2-[4-(6-methoxy-3-indolyl)-3-thiabutyl]-
2-[4-(7-methoxy-3-indolyl)-3-thiabutyl]-
2-[4-(5-fluoro-3-indolyl)-3-thiabutyl]-
2-[4-(6-fluoro-3-indolyl)-3-thiabutyl]-
2-[4-(5-chloro-3-indolyl)-3-thiabutyl]-
2-[4-(6-chloro-3-indolyl)-3-thiabutyl]-
2-[4-(5-bromo-3-indolyl)-3-thiabutyl]-
2-[4-(6-bromo-3-indolyl)-3-thiabutyl]-;
and the following 9-oxo-1,2,3,4-tetrahydro-2-azafluorenes:
2-[4-(3-indolyl)-3-thiabutyl]-
2-[4-(4-cyano-3-indolyl)-3-thiabutyl]-
2-[4-(5-cyano-3-indolyl)-3-thiabutyl]-
2-[4-(6-cyano-3-indolyl)-3-thiabutyl]-
2-[4-(7-cyano-3-indolyl)-3-thiabutyl]-
2-[4-(4-methoxycarbonyl-3-indolyl)-3-thiabutyl]-
2-[4-(5-methoxycarbonyl-3-indolyl)-3-thiabutyl]-
2-[4-(6-methoxycarbonyl-3-indolyl)-3-thiabutyl]-
2-[4-(7-methoxycarbonyl-3-indolyl)-3-thiabutyl]-
2-[4-(4-ethoxycarbonyl-3-indolyl)-3-thiabutyl]-
2-[4-(5-ethoxycarbonyl-3-indolyl)-3-thiabutyl]-
2-[4-(6-ethoxycarbonyl-3-indolyl)-3-thiabutyl]-
2-[4-(7-ethoxycarbonyl-3-indolyl)-3-thiabutyl]-
2-[4-(4-carbamoyl-3-indolyl)-3-thiabutyl]-
2-[4-(5-carbamoyl-3-indolyl)-3-thiabutyl]-
2-[4-(6-carbamoyl-3-indolyl)-3-thiabutyl]-
2-[4-(7-carbamoyl-3-indolyl)-3-thiabutyl]-
2-[4-(4-methoxy-3-indolyl)-3-thiabutyl]-
2-[4-(5-methoxy-3-indolyl)-3-thiabutyl]-
2-[4-(6-methoxy-3-indolyl)-3-thiabutyl]-
2-[4-(7-methoxy-3-indolyl)-3-thiabutyl]-
2-[4-(5-fluoro-3-indolyl)-3-thiabutyl]-
2-[4-(6-fluoro-3-indolyl)-3-thiabutyl]-
2-[4-(5-chloro-3-indolyl)-3-thiabutyl]-
2-[4-(6-chloro-3-indolyl)-3-thiabutyl]-
2-[4-(5-bromo-3-indolyl)-3-thiabutyl]-
2-[4-(6-bromo-3-indolyl)-3-thiabutyl]-.

EXAMPLE 18

A solution of 5.09 g of 2-[4-(5-dimethyl-tert.-butylsilyloxy-3-indolyl)-3-thiabutyl]-1,2,3,4-tetrahydrobenzothieno[2,3-c]pyridine [obtainable by etherification of 5-hydroxyindole to give 5-dimethyl-tert.-butylsilyloxyindole (Rf 0.46, dichloromethane), Mannich reaction to give 5-dimethyl-tert.-butylsilyloxygramine (hydrochloride, m.p. 156°–157°) and reaction with 2-(2-mercaptoethyl)-1,2,3,4-tetrahydrobenzothieno[2,3-c]pyridine] and 1.16 g of KF in 200 ml of methanol is allowed to stand at 20° for 16 hours. After the usual working up, 2-[4-(5-hydroxy-3-indolyl)-3-thiabutyl]-1,2,3,4-tetrahydrobenzothieno[2,3-c]pyridine is obtained.

The following 1,2,3,4-tetrahydrobenzothieno[2,3-c]pyridines are obtained analogously from 4-, 6- or 7-hydroxyindole via 4- (Rf. 0.52, dichloromethane), 6- (Rf. 0.50, dichloromethane) or 7-dimethyl-tert.-butylsilyloxyindole, 4-(hydrochloride, m.p. 168°–170°), 6-(hydrochloride, m.p. 161°–162°), or 7-dimethyl-tert.-butylsilyloxygramine and 2-[4-(4-, 2-[4-(6- or 2-[4-(7-dimethyl-tert.-butylsilyloxy-3-indolyl)-3-thiabutyl]-1,2,3,4-tetrahydrobenzothieno[2,3-c]pyridine:
2-[4-(4-hydroxy-3-indolyl)-3-thiabutyl]-
2-[4-(6-hydroxy-3-indolyl)-3-thiabutyl]-
2-[4-(7-hydroxy-3-indolyl)-3-thiabutyl]-.
With the appropriate starting materials of the formula IIIa, the following 1,2,3,4-tetrahydrobenzofuro[2,3-c]pyridines are obtained analogously:
2-[4-(4-hydroxy-3-indolyl)-3-thiabutyl]-
2-[4-(5-hydroxy-3-indolyl)-3-thiabutyl]-
2-[4-(6-hydroxy-3-indolyl)-3-thiabutyl]-
2-[4-(7-hydroxy-3-indolyl)-3-thiabutyl]-;
and the following 1,2,3,4,5,6-hexahydrobenzo[f]isoquinolines:
2-[4-(4-hydroxy-3-indolyl)-3-thiabutyl]-
2-[4-(5-hydroxy-3-indolyl)-3-thiabutyl]-
2-[4-(6-hydroxy-3-indolyl)-3-thiabutyl]-
2-[4-(7-hydroxy-3-indolyl)-3-thiabutyl]-;
and the following 1,2,3,4-tetrahydro-2-azafluorenes:
2-[4-(4-hydroxy-3-indolyl)-3-thiabutyl]-
2-[4-(5-hydroxy-3-indolyl)-3-thiabutyl]-
2-[4-(6-hydroxy-3-indolyl)-3-thiabutyl]-
2-[4-(7-hydroxy-3-indolyl)-3-thiabutyl]-
2-[4-(4-hydroxy-3-indolyl)-3-thiabutyl]-9-hydroxy-
2-[4-(5-hydroxy-3-indolyl)-3-thiabutyl]-9-hydroxy-
2-[4-(6-hydroxy-3-indolyl)-3-thiabutyl]-9-hydroxy-
2-[4-(7-hydroxy-3-indolyl)-3-thiabutyl]-9-hydroxy-
2-[4-(4-hydroxy-3-indolyl)-3-thiabutyl]-9-oxo-
2-[4-(5-hydroxy-3-indolyl)-3-thiabutyl]-9-oxo-
2-[4-(6-hydroxy-3-indolyl)-3-thiabutyl]-9-oxo-
2-[4-(7-hydroxy-3-indolyl)-3-thiabutyl]-9-oxo-.

EXAMPLE 19

A mixture of 3.9 g of 2-[4-(5-methoxy-3-indolyl)-butyl]-1,2,3,4-tetrahydrobenzothieno[2,3-c]pyridine and 3.5 g of pyridine hydrochloride is stirred at 160° for 3 hours. After the usual working up, 2-[4-(5-hydroxy-3-indolyl)butyl]-1,2,3,4-tetrahydrobenzothieno[2,3-c]pyridine is obtained.

EXAMPLE 20

37.4 g of 2-[4-(5-hydroxymethyl-3-indolyl)butyl]-1,2,3,4-tetrahydrobenzofuro[2,3-c]pyridine are dissolved in 1.6 l of THF, and 300 ml of ether are added. While stirring, 55 g of MnO$_2$ are added. The mixture is stirred at 20° for 16 hours, a further 100 g of MnO$_2$ are added in portions, and the mixture is stirred at 20° for a further 100 hours. After filtration and the usual working up, 2-[4-(5-formyl-3-indolyl)butyl]-1,2,3,4-tetrahydrobenzofuro[2,3-c]pyridine is obtained.

EXAMPLE 21

3.74 g of 2-[4-(5-hydroxymethyl-3-indolyl)-butyl]-1,2,3,4-tetrahydrobenzofuro[2,3-c]pyridine are dissolved in 50 ml of dichloromethane, 9 g of MnO$_2$ are added to the solution, the mixture is stirred at 40° for 60 hours, and the insolubles are filtered off. After the usual working up of the filtrate, 2-[4-(5-carboxy-3-indolyl)butyl]-1,2,3,4-tetrahydrobenzofuro[2,3-c]pyridine is obtained.

EXAMPLE 22

3.72 g of 2-[4-(5-formyl-3-indolyl)butyl]-1,2,3,4-tetrahydrobenzofuro[2,3-c]pyridine are dissolved in 80 ml of dichloromethane, 9 g of MnO$_2$ are added, and the suspension is stirred at 40° for 48 hours. After filtration and the usual working up, 2-[4-(5-carboxy-3-indolyl)butyl]-1,2,3,4-tetrahydrobenzofuro[2,3-c]pyridine is obtained.

EXAMPLE 23

3.88 g of 2-[4-(5-carboxy-3-indolyl)butyl]-1,2,3,4-tetrahydrobenzofuro[2,3-c]pyridine are suspended in 25 ml of toluene and, under N$_2$ and while stirring, 3 times the molar amount of a 20% solution of diisobutylaluminium hydride in toluene is added dropwise, and the mixture is boiled for 2 hours, cooled, decomposition is carried out with water, the usual working up is carried out, and 2-[4-(5-formyl-3-indolyl)butyl]-1,2,3,4-tetrahydrobenzofuro[2,3-c]pyridine is obtained.

EXAMPLE 24

A solution of 3.88 g of 2-[4-(5-carboxy-3-indolyl)-butyl]-1,2,3,4-tetrahydrobenzofuro[2,3-c]pyridine in 40 ml of THF is added dropwise to a stirred suspension of 0.76 g of lithium aluminium hydride in 30 ml of THF under N$_2$. The mixture is then stirred at 20° for 2 hours, decomposition is carried out with dilute sodium hydroxide solution and then with water, and the mixture is filtered. The usual working up is carried out on the filtrate. 2-[4-(5-Hydroxymethyl-3-indolyl)butyl]-1,2,3,4-tetrahydrobenzofuro[2,3-c]pyridine is obtained.

EXAMPLE 25

A solution of 4.18 g of 2-[4-(5-methoxycarbonyl-3-indolyl)butyl]-1,2,3,4-tetrahydrobenzothieno[2,3c]pyridine in 40 ml of THF is added dropwise to a stirred suspension of 0.57 g of lithium aluminium hydride in 20 ml of THF at 20° under N$_2$. The mixture is stirred at 20° for 1 hour, and decomposition is carried out with dilute sodium hydroxide solution and then with water, and the mixture is filtered, the usual working up is carried out on the filtrate, and 2-[4-(5-hydroxymethyl-3-indolyl)butyl]-1,2,3,4-tetrahydrobenzothieno[2,3-c]pyridine is obtained.
The following are obtained analogously by reduction of the corresponding esters:
2-[4-(4-hydroxymethyl-3-indolyl)butyl]-1,2,3,4-tetrahydrobenzothieno[2,3-c]pyridine
2-[4-(6-hydroxymethyl-3-indolyl)butyl]-1,2,3,4-tetrahydrobenzothieno[2,3-c]pyridine
2-[4-(7-hydroxymethyl-3-indolyl)butyl]-1,2,3,4-tetrahydrobenzothieno[2,3c]pyridine
2-[4-(4-hydroxymethyl-3-indolyl)butyl]-1,2,3,4-tetrahydrobenzofuro[2,3c]pyridine
2-[4-(5-hydroxymethyl-3-indolyl)butyl]-1,2,3,4-tetrahyrobenzofuro[2,3-c]pyridine
2-[4-(6-hydroxymethyl-3-indolyl)butyl]-1,2,3,4-tetrahydrobenzofuro[2,3-c]pyridine
2-[4-(7-hydroxymethyl-3-indolyl)butyl]-1,2,3,4-tetrahydrobenzofuro[2,3-c]pyridine
3-[4-(4-hydroxymethyl-3-indolyl)butyl]-1,2,3,4,5,6-hexahydrobenzo[f]isoquinoline
3-[4-(5-hydroxymethyl-3-indolyl)butyl]-1,2,3,4,5,6-hexahydrobenzo[f]isoquinoline
3-[4-(6-hydroxymethyl-3-indolyl)butyl]-1,2,3,4,5,6-hexahydrobenzo[f]isoquinoline
3-[4-(7-hydroxymethyl-3-indolyl)butyl]-1,2,3,4,5,6-hexahydrobenzo[f]isoquinoline
2-[4-(4-hydroxymethyl-3-inolyl)butyl]-1,2,3,4-tetrahydro-2-azafluorene 2-[4-(5-hydroxymethyl-3-indolyl)butyl]-1,2,3,4-tetrahydro-2-azafluorene
2-[4-(6-hydroxymethyl-3-indolyl)butyl]-1,2,3,4-tetrahydro-2-azafluorene
2-[4-(7-hydroxymethyl-3-indolyl)butyl]-1,2,3,4-tetrahydro-2-azafluorene
2-[4-(4-hydroxymethyl-3-indolyl)butyl]-9-hydroxy-1,2,3,4-tetrahydro-2-azafluorene
2-[4-(5-hydroxymethyl-3-indolyl)butyl]-9-hydroxy-1,2,3,4-tetrahydro-2-azafluorene
2-[4-(6-hydroxymethyl-3-indolyl)butyl]-9-hydroxy-1,2,3,4-tetrahydro-2-azafluorene
2-[4-(7-hydroxymethyl-3-indolyl)butyl]-9-hydroxy-1,2,3,4-tetrahydro-2-azafluorene
2-[4-(4-hydroxymethyl-3-indolyl)-3-thiabutyl]-1,2,3,4-tetrahydrobenzothieno[2,3-c]pyridine
2-[4-(5-hydroxymethyl-3-indolyl)-3-thiabutyl]-1,2,3,4-tetrahydrobenzothieno[2,3-c]pyridine
2-[4-(6-hydroxymethyl-3-indolyl)-3-thiabutyl]-1,2,3,4-tetrahydrobenzothieno[2,3-c]pyridine
2-[4-(7-hydroxymethyl-3-indolyl)-3-thiabutyl]-1,2,3,4-tetrahydrobenzothieno[2,3-c]pyridine
2-[4-(4-hydroxymethyl-3-indolyl)-3-thiabutyl]-1,2,3,4-tetrahydrobenzofuro[2,3-c]pyridine
2-[4-(5-hydroxymethyl-3-indolyl)-3-thiabutyl]-1,2,3,4-tetrahydrobenzofuran[2,3-c]pyridine
2-[4-(6-hydroxymethyl-3-indolyl)-3-thiabutyl]-1,2,3,4-tetrahydrobenzofuro[2,3-c]pyridine
2-[4-(7-hydroxymethyl-3-indolyl)-3-thiabutyl]-1,2,3,4-tetrahydrobenzofuro[2,3-c]pyridine
3-[4-(4-hydroxymethyl-3-indolyl)-3-thiabutyl]-1,2,3,4,5,6-hexahydrobenzo[f]isoquinoline
3-[4-(5-hydroxymethyl-3-indolyl)-3-thiabutyl]-1,2,3,4,5,6-hexahydrobenzo[f]isoquinoline
3-[4-(6-hydroxymethyl-3-indolyl)-3-thiabutyl]-1,2,3,4,5,6-hexahydrobenzo[f]isoquinoline
3-[4-(7-hydroxymethyl-3-indolyl)-3-thiabutyl]-1,2,3,4,5,6-hexahydrobenzo[f]isoquinoline
2-[4-(4-hydroxymethyl-3-indolyl)-3-thiabutyl]-1,2,3,4-tetrahydro-2-azafluorene
2-[4-(5-hydroxymethyl-3-indolyl)-3-thiabutyl-1,2,3,4-tetrahydro-2-azafluorene
2-[4-(6-hydroxymethyl-3-indolyl)-3-thiabutyl]-1,2,3,4-tetrahydro-2-azafluorene
2-[4-(7-hydroxymethyl-3-indolyl)-3-thiabutyl]-1,2,3,4-tetrahydro-2-azafluorene
2-[4-(4-hydroxymethyl-3-indolyl)--thiabutyl]-9-hydroxy-1,2,3,4-tetrahydro-2-azafluorene
2-[4-(5-hydroxymethyl-3-indolyl)-3-thiabutyl]-9-hydroxy-1,2,3,4-tetrahydro-2-azafluorene
2-[4-(6-hydroxymethyl-3-indolyl)-3-thiabutyl]-9-hydroxy-1,2,3,4-tetrahydro-2-azafluorene
2-[4-(7-hydroxymethyl-3-indolyl)-3-thiabutyl]-9-hydroxy-1,2,3,4-tetrahydro-2-azafluorene.

EXAMPLE 26

A solution of 3.84 g of 3-[4-(6-formyl-3-indolyl)-butyl]-1,2,3,4,5,6-hexahydrobenzo[f]isoquinoline in 40 ml of THF is added dropwise to a stirred suspension of 0.57 g of lithium aluminium hydride in 20 ml of THF under N$_2$. The mixture is then stirred at 20° for 1 hour, and decomposition is carried out with dilute sodium hydroxide solution and then with water, and the mixture is filtered and the usual working up is carried out, and 3-[4-(6-hydroxymethyl-3-indolyl)butyl]-1,2,3,4,5,6-hexahydrobenzo[f]isoquinoline is obtained.

EXAMPLE 27

HCl is passed for 2 hours into a solution of 3.88 g of 2-[4-(5-carboxy-3-indolyl)butyl]-1,2,3,4-tetrahydrobenzofuro[2,3-c]pyridine in 50 ml of absolute ethanol. The mixture is then allowed to stand at 20° for 48 hours, the usual working up is carried out, and 2-[4-(5-ethoxycarbonyl-3-indolyl)butyl]-1,2,3,4-tetrahydrobenzofuro[2,3-c]pyridine is obtained.

EXAMPLE 28

1.8 g of N,N'-carbonyldiimidazole are added to a solution of 4 g of 3-[4-(5-carboxy-3-indolyl)butyl]-1,2,3,4,5,6-hexahydrobenzo[f]isoquinoline in 40 ml of DMF, and the mixture is stirred at 20° for 2 hours, then 0.6 g of NH$_4$Cl is added, and the mixture is heated at 40° for 3 hours. After the usual working up 3-[4-(5-carbamoyl-3-indolyl)butyl]-1,2,3,4,5,6-hexahydrobenzo[f]isoquinoline is obtained.

EXAMPLE 29

3.88 g of 2-[4-(5-carboxy-3-indolyl)butyl]-1,2,3,4-tetrahydrobenzofuro[2,3-c]pyridine are dissolved in 30 ml of chloroform, the solution is saturated with HCl gas, 1.8 g of thionyl chloride are added dropwise, and the mixture is boiled for 2 hours. Evaporation is carried out, 30 ml of toluene are added, evaporation is repeated, and the resulting crude acid chloride is dissolved in 20 ml of chloroform, and this solution is added dropwise to a stirred saturated solution of ammonia in 50 ml of chloroform, and the mixture is stirred at 20° for 2 hours, filtered and the filtrate is concentrated. After the usual working up 2-[4-(5-carbamoyl-3-indolyl)butyl]-1,2,3,4-tetrahydrobenzofuro[2,3-c]pyridine is obtained.

EXAMPLE 30

0.02 mol of concentrated ammonia (D=0.9) is added dropwise to a solution of 4.02 g of 2-[4-(5-methoxycarbonyl-3-indolyl)butyl]-1,2,3,4-tetrahydrobenzofuro[2,3-c]pyridine in 30 ml of dimethylformamide at 20°. The mixture is stirred at 20° for 1 hour, the usual working up is carried out and 2-[4-(5-carbamoyl-3-indolyl)butyl]-1,2,3,4-tetrahydrobenzofuro[2,3-c]pyridine is obtained.

EXAMPLE 31

A mixture of 38.7 g of 2-[4-(5-carbamoyl-3-indolyl)-butyl]-1,2,3,4-tetrahydrobenzofuro[2,3-c]pyridine, 27.1 g of NaOH, 525 ml of water and 450 ml of diethylene glycol monoethyl ether is boiled, with stirring, for 16 hours. The mixture is cooled, the usual working up followed by acidification is carried out, and 2-[4-(5-carboxy-3-indolyl)butyl]-1,2,3,4-tetrahydrobenzofuro[2,3-c]pyridine is obtained.

EXAMPLE 32

4.16 g of 2-[4-(5-ethoxycarbonyl-3-indolyl)butyl]-1,2,3,4-tetrahydrobenzofuro[2,3-c]pyridine are boiled with 20 ml of water and 100 ml of 2N ethanolic KOH for 30 min, the usual working up is carried out, and 2-[4-(5-carboxy-3-indolyl)butyl]-1,2,3,4-tetrahydrobenzofuro[2,3-c]pyridine is obtained.

EXAMPLE 33

In analogy to Example 1 3-[4-(3-indolyl)-butyl]-1,2,3,4-tetrahydro-benzo[f]isoquinoline is obtained from 1,2,3,4-tetrahydrobenzo[f]isoquinoline.

Analogously, the following 1,2,3,4-tetraydrobenzo[f]isoquinolines are obtained:

2-[2-(3-indolyl)ethyl]-
2-[3-(3-indolyl)propyl]-
3-[4-(5,6-methylenedioxy-3-indolyl)-butyl]-
2-[4-(4-cyano-3-indolyl)butyl]-
2-[4-(5-cyano-3-indolyl)butyl]-
2-[4-(6-cyano-3-indolyl)butyl]-
2-[4-(7-cyano-3-indolyl)butyl]-
2-[4-(4-methoxycarbonyl-3-indolyl)butyl]-
2-[4-(5-methoxycarbonyl-3-indolyl)butyl]-
2-[4-(6-methoxycarbonyl-3-indolyl)butyl]-
2-[4-(7-methoxycarbonyl-3-indolyl)butyl]-
2-[4-(4-ethoxycarbonyl-3-indolyl)butyl]-
2-[4-(5-ethoxycarbonyl-3-indolyl)butyl]-
2-[4-(6-ethoxycarbonyl-3-indolyl)butyl]-
2-[4-(7-ethoxycarbonyl-3-indolyl)butyl]-
2-[4-(4-carbamoyl-3-indolyl)butyl]-
2-[4-(5-carbamoyl-3-indolyl)butyl]-
2-[4-(6-carbamoyl-3-indolyl)butyl]-
2-[4-(7-carbamoyl-3-indolyl)butyl]-
2-[4-(5-N-methylcarbamoyl-3-indolyl)butyl]-
2-[4-(5-N,N-dimethylcarbamoyl-3-indolyl)butyl]-
2-[4-(1-methyl-3-indolyl)butyl]-
2-[4-(2-methyl-3-indolyl)butyl]-
2-[4-(5-methyl-3-indolyl)butyl]-
2-[4-(4-methoxy-3-indolyl)butyl]-
2-[4-(5-methoxy-3-indolyl)butyl]-
2-[4-(6-methoxy-3-indolyl)butyl]-
2-[4-(7-methoxy-3-indolyl)butyl]-
2-[4-(5,6-dimethoxy-5-indolyl)butyl]-
2-[4-(4-hydroxy-3-indolyl)butyl]-
2-[4-(5-hydroxy-5-indolyl)butyl]-
2-[4-(6-hydroxy-3-indolyl)butyl]-
2-[4-(7-hydroxy-3-indolyl)butyl]-
2-[4-(5,6-dihydroxy-3-indolyl)butyl]-
2-[4-(5-fluoro-3-indolyl)butyl]-
2-[4-(6-fluoro-3-indolyl)butyl]-
2-[4-(5-chloro-3-indolyl)butyl]-
2-[4-(6-chloro-3-indolyl)butyl]-
2-[4-(5-bromo-3-indolyl)butyl]-
2-[4-(6-bromo-3-indolyl)butyl]-
2-[5-(3-indolyl)pentyl]-.

The examples which follow relate to the pharmaceutical compositions which contain compounds of the formula I or their physiologically acceptable salts:

EXAMPLE A

Tablets

A mixture of 1 kg of 2-[4-(5-hydroxy-3-indolyl)-butyl]-1,2,3,4-tetrahydrobenzothieno[2,3-c]pyridine, 4 kg of lactose, 1.2 kg of potato starch, 0.2 kg of talc and 0.1 kg of magnesium stearate is compressed in the customary manner to give tablets so that each tablet contains 10 mg of active compound.

EXAMPLE B

Coated Tablets

Tablets are formed by compression in analogy to Example A and are then coated in a customary manner with a coating comprising sucrose, potato starch, talc, tragacanth and colorant.

EXAMPLE C

Capsules 2 kg of 2-[4-(5-hydroxy-3-indolyl)butyl]-1,2,3,4-tetrahydrobenzofuro[2,3-c]pyridine are dispensed into hard gelatin capsules in the customary manner so that each capsule contains 20 mg of the active compound.

EXAMPLE D

Ampoules

A solution of 1 kg of 3-[4-(5-hydroxy-3-indolyl)-butyl]-1,2,3,4,5,6-hexahydrobenzo[f]isoquinoline hydrochloride in 60 l of double-distilled water is sterilized by filtration, dispensed into ampoules, freeze-dried under sterile conditions and sealed sterile. Each ampoule contains 10 mg of active compound.

Tablets, coated tablets, capsules and ampoules which contain one or more of the other active compounds of the formula I and/or of their physiologically acceptable acid addition salts can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An indole derivative of the formula

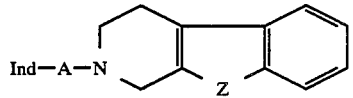

wherein

Ind is 3-indolyl or 3-indolyl substituted by (a) a hydroxymethyl, methylenedioxy, S-alkyl, SO-alkyl, SO$_2$-alkyl, CN or COW group, or (b) substituted once or twice by alkyl, O-alkyl, OH, F, Cl or Br, or (c) a combination of (a) and (b), W is H, OH, O-alkyl, NH$_2$, NH-alkyl or N(alkyl)$_2$, A is —(CH$_2$)$_n$—, —CH$_2$—S—CH$_2$CH$_2$—, —CH$_2$—SO—CH$_2$CH$_2$— or —CH$_2$—SO$_2$—CH$_2$CH$_2$—, Z is —(CH$_2$)$_m$—, —CH=CH—, —CHOH—, —CO—, S, SO, SO$_2$ or O, n is 2, 3, 4 or 5 and m is 1, 2 or 3, each alkyl group independently is of 1–4C atoms, or a physiologically acceptable salt thereof.

2. A compound of claim 1, wherein Ind is hydroxy-3-indolyl, methoxy-3-indolyl or 3-indolyl.

3. A compound of claim 1, wherein Ind is 5- or 6-hydroxy-3-indolyl, 5- or 6-methoxy-3-indolyl or 3-indolyl.

4. A compound of claim 1, wherein A is —(CH$_2$)$_n$— or —CH$_2$—S—CH$_2$CH$_2$—.

5. A compound of claim 1, wherein A is —(CH$_2$)$_4$—.

6. A compound of claim 1, wherein Z is —(CH$_2$)$_2$ or —CH=CH—.

7. A compound of claim 1, wherein Z is —CHOH—.

8. A compound of claim 1, wherein Z is S.

9. A compound of claim 1, wherein Z is O.

10. A compound of claim 1, wherein

Ind is 5- or 6-hydroxy-3-indolyl, 5- or 6-methoxy-3-indolyl or 3-indolyl,

A is —(CH$_2$)$_n$— or —CH$_2$—S—CH$_2$CH$_2$— and

Z is —(CH$_2$)$_2$.

11. A compound of claim 1, wherein

Ind is 5- or 6-hydroxy-3-indolyl, 5- or 6-methoxy-3-indolyl or 3-indolyl,
A is $-(CH_2)_n-$ or $-CH_2-S-CH_2CH_2-$ and
Z is $-CHOH$.

12. A compound of claim 1, wherein
Ind is 5- or 6-hydroxy-3-indolyl, 5- or 6-methoxy-3-indolyl,
A is $-(CH_2)_n-$ or $-CH_2-S-CH_2CH_2-$ and
Z is S.

13. A compound of claim 1, wherein
Ind is 5- or 6-hydroxy-3-indolyl, 5- or 6-methoxy-3-indolyl, or 3-indolyl,
A is $-(CH_2)_n-$ or $-CH_2-S-CH_2CH_2-$ and
Z is O.

14. 2-[4-(5-Hydroxy-3-indolyl)butyl]-1,2,3,4-tetrahydrobenzothieno[2,3-c]pyridine, a compound of claim 1.

15. 2-[4-(5-Hydroxy-3-indolyl)butyl]-1,2,3,4-tetrahydrobenzofuro[2,3-c]pyridine, a compound of claim 1.

16. 3-[4-(5-Hydroxy-3-indolyl)butyl]-1,2,3,4,5,6-hexahydrobenzo[f]isoquinoline, a compound of claim 1.

17. A pharmaceutical comoposition comprising an effective amount of at least one compound of claim 1 and a physiologically acceptable carrier.

18. A pharmaceutical composition comprising 0.2-500 mg of a compound of claim 1 and a pharmaceutically acceptable carrier.

19. A method of treating migraine comprising administering to a patient in need of such treatment an amount effective to treat said migraine of a compound of claim 1.

20. A method of treating parkinsonism, comprising administering to a patient in need of such treatment an amount effective to treat said parkinsonism of a compound of claim 1.

21. A method of treating depression comprising administering to a patient in need of such treatment an antidepressantly effective amount of a compound of claim 1.

22. A method of treating psychosis comprising administering to a patient in need of such treatment an antipsychotic effective amount of a compound of claim 1.

* * * * *